US006790649B1

United States Patent
Crine et al.

(10) Patent No.: US 6,790,649 B1
(45) Date of Patent: Sep. 14, 2004

(54) COMPOSITION, METHODS AND REAGENTS FOR THE SYNTHESIS OF A SOLUBLE FORM OF HUMAN PHEX

(75) Inventors: Philippe Crine, Outremont (CA); Guy Boileau, Brossard (CA)

(73) Assignee: Universite De Montreal, Montreal (CA)

( * ) Notice: Subject to any disclaimer, the term of this patent is extended or adjusted under 35 U.S.C. 154(b) by 0 days.

(21) Appl. No.: 09/913,955

(22) PCT Filed: Feb. 24, 2000

(86) PCT No.: PCT/CA00/00201

§ 371 (c)(1),
(2), (4) Date: Aug. 21, 2001

(87) PCT Pub. No.: WO00/50580

PCT Pub. Date: Aug. 31, 2000

(30) Foreign Application Priority Data

Feb. 24, 1999 (CA) .............................................. 2262056

(51) Int. Cl.[7] .............................. C12N 9/48; C12Q 1/34; C12Q 1/37; C07H 21/04; C07K 17/00
(52) U.S. Cl. ............................ 435/212; 435/18; 435/24; 435/440; 435/455; 435/195; 435/325; 435/320.1; 435/69.1; 536/23.2; 530/350
(58) Field of Search ......................... 435/18, 24, 440, 435/455, 195, 212, 325, 320.1, 69.1; 536/23.2; 530/350

(56) References Cited

U.S. PATENT DOCUMENTS 5,840,509 A * 11/1998 Ni et al. ....................... 435/23

FOREIGN PATENT DOCUMENTS

WO    WO 98/10078    3/1998

OTHER PUBLICATIONS

Guo et al., Journal of Bone and Mineral Research 12:1009–1017, 1997.*
Bork, Genome Research, 10:398–400, 2000.*
Broun et al., Science 282:1315–1317, 1998.*
Seffernick et al., J. Bacteriol. 183(8):2405–2410, 2001.*
Van de Loo et al., Proc. Natl. Acad. Sci. 92:6743–6747, 1995.*
Witkowski et al., Biochemistry 38:11643–11650, 1999.
Lipman et al, "Cloning of Human PEX cDNA," The Journal of Biological Chemistry, vol. 273, No. 22, pp.13729–13737 (1998).
Devault et al, "Expression of Neutral Endopeptidase . . . ," The Journal of Biological Chemistry, vol. 263, No. 8, pp. 4033–4040. (1988).
Lemay et al, "Fusion of a Cleavable Signal Peptide. . . ," The Journal of Biological Chemistry, vol. 264, No. 26, pp. 15620–15623. (1989).
Korth et al, "Construction, expression and characterization of . . . ," FEBS Letters 417, pp. 365–370 (1997).
Helene et al, "Effects of Monoclonal Antibodies Raised. . . ," Biochemical Pharmacology, vol. 43, No. 4, pp. 809–814 (1992).
Fenton et al, "Long–Term Culture of Disaggregated Rat. . .,", Journal of Cellular Physiology, vol. 155, pp. 1–7 (1993).

* cited by examiner

*Primary Examiner*—Rebecca E. Prouty
*Assistant Examiner*—Delia Ramirez
(74) *Attorney, Agent, or Firm*—Nixon & Vanderhye

(57) ABSTRACT

This invention relates to a soluble form of PHEX, PHEX being a type II integral membrane glycoprotein. This enzyme is the gene product of a phosphate-regulating gene with homologies to endopeptidases on the X chromosome. To produce a soluble form of PHEX, the transmembrane anchor domain has been modified to encode a signal peptidase coding sequence. The soluble PHEX therefore comprises the active ectodomain. An inactive mutant of PHEX is also an object of this invention. Both soluble and inactive mutant forms of PHEX can be used to screen ligands to PHEX. These ligands can also be used as substrates or inhibitors of PHEX. PHEX being phosphaturic, an inhibitor thereof will be used to treat phosphaturia and/or hypophosphatemia. On the opposite, a substrate for PHEX or PHEX itself can be used to treat hyperphosphatemia.

7 Claims, 8 Drawing Sheets

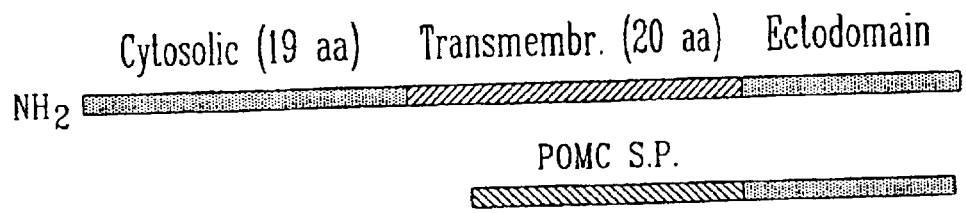
FIG. 1A
| VGGTLVLGTILFLVSQGLLS | 1 |
| VLTVIAQQTTLFLVSQGLLS | 2 |
| VLTVIAQQTT    SQGLLS | 3 |
FIG. 1B

```
  1  MEAETGSSVE TGKKANRGTR IAIVVEVGGT LVLGTILFLV SQGLLSLQAK QEYCLKPECI
 61  EAAAAILSKV NLSVDPCDNF FRFACDGWIS NNPIPEDMPS YGVYPWLRHN VDLKLKELLE
121  KSISRRRDTE AIQKAKILYS SCMNEKAIEK ADAKPLLHIL RHSPFRWPVL ESNIGPEGVW
181  SERKFSLLQT LATERGQYSN SVFIRLYVSP DDKASNEHIL KLDQATLSLA VREDYLDNST
241  EAKSYRDALY KFMVDTAVLL GANSSRAEHD MKSVLRLEIK IAEIMIPHEN RTSEAMYNKM
301  NISELSAMIP QFDWLGYIKK VIDTRLYPHL KDISPSENVV VRVPQYFKDL FRILGSERKK
361  TIANYLVWRM VYSRIPNLSR REQYRWLEFS RVIQGTTTLL PQWDKCVNFI ESALPYVVGK
421  MFVDVYFQED KKEMMEELVE GVRWAFIDML EKENEWMDAG TKRKAKEKAR AVLAKVGYPE
481  FIMNDTHVNE DLKAIKFSEA DYFGNVLQTR KYLAQSDFFW LRKAVPKTEW FTNPTTVNAF
541  YSASTNQIRF PAGELQKPEF WGTEYPRSLS YGAIGVIVGH EFTHGFDNNG RKYDKNGNLD
601  PWWSTESEEK FKEKTKCMIN QYSNYYWKKA GLNVKGKRTL GENIADNGGL REAFRAYRKW
661  INDRRQGLEE PLLPGITFTN NQLFFLSYAH VRCNSYRPEA AREQVQIGAH SPPQFRVNGA
721  ISNSEEFQKA FNCPPNSTMN RGMDSCRLW
```

FIG. 2

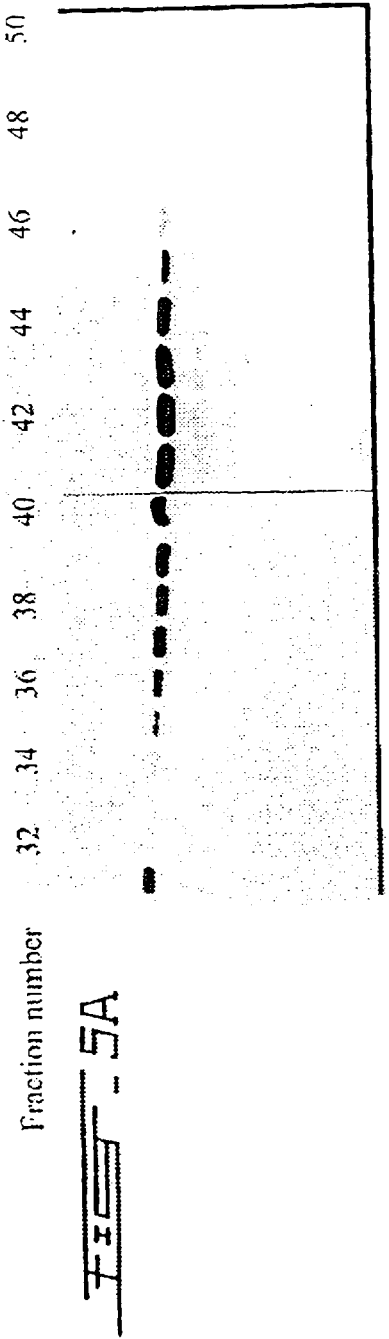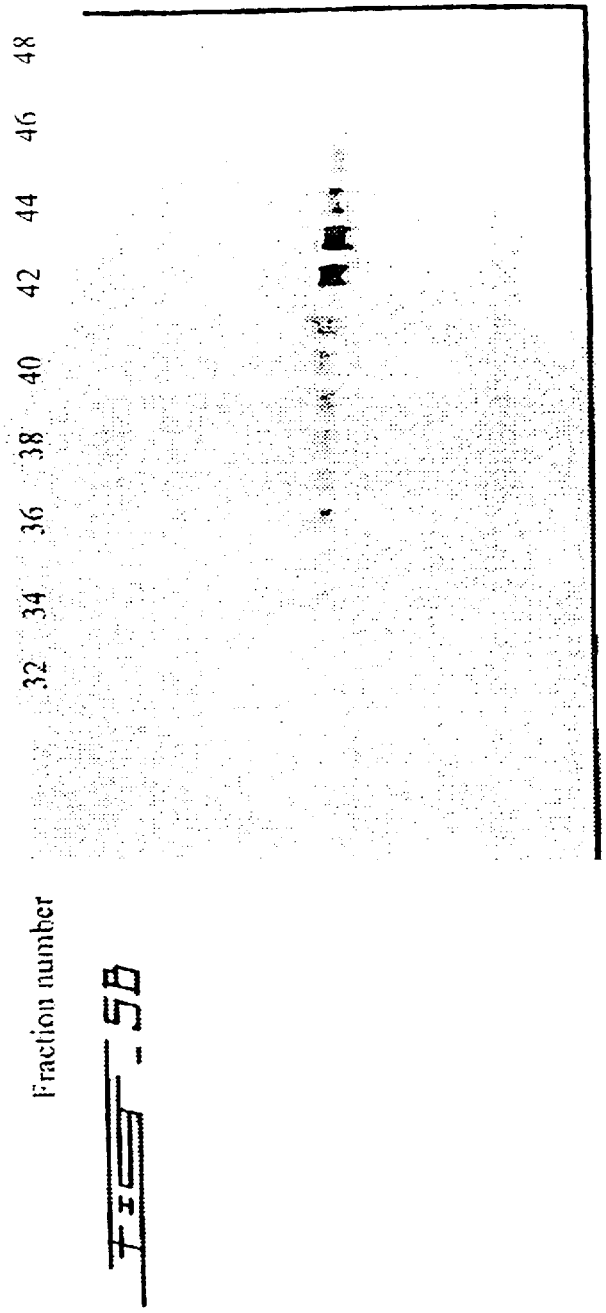
FIG-5A
FIG-5B

SEQUENCE LISTING

```
<160> NUMBER OF SEQ ID NOS: 6

<210> SEQ ID NO 1
<211> LENGTH: 749
<212> TYPE: PRT
<213> ORGANISM: Homo sapiens

<400> SEQUENCE: 1

Met Glu Ala Glu Thr Gly Ser Ser Val Glu Thr Gly Lys Lys Ala Asn
 1               5                  10                  15

Arg Gly Thr Arg Ile Ala Leu Val Val Phe Val Gly Gly Thr Leu Val
            20                  25                  30

Leu Gly Thr Ile Leu Phe Leu Val Ser Gln Gly Leu Leu Ser Leu Gln
        35                  40                  45

Ala Lys Gln Glu Tyr Cys Leu Lys Pro Glu Cys Ile Glu Ala Ala Ala
    50                  55                  60

Ala Ile Leu Ser Lys Val Asn Leu Ser Val Asp Pro Cys Asp Asn Phe
65                  70                  75                  80

Phe Arg Phe Ala Cys Asp Gly Trp Ile Ser Asn Asn Pro Ile Pro Glu
                85                  90                  95

Asp Met Pro Ser Tyr Gly Val Tyr Pro Trp Leu Arg His Asn Val Asp
            100                 105                 110

Leu Lys Leu Lys Glu Leu Leu Glu Lys Ser Ile Ser Arg Arg Arg Asp
        115                 120                 125

Thr Glu Ala Ile Gln Lys Ala Lys Ile Leu Tyr Ser Ser Cys Met Asn
    130                 135                 140
```

-continued

| | | | | | | | | | | | |
|---|---|---|---|---|---|---|---|---|---|---|---|
| Glu | Lys | Ala | Ile | Glu | Lys | Ala | Asp | Ala | Lys | Pro | Leu | Leu | His | Ile | Leu |
| 145 | | | | 150 | | | | 155 | | | | 160 |

Glu Lys Ala Ile Glu Lys Ala Asp Ala Lys Pro Leu Leu His Ile Leu
145                 150                 155                 160

Arg His Ser Pro Phe Arg Trp Pro Val Leu Glu Ser Asn Ile Gly Pro
                165                 170                 175

Glu Gly Val Trp Ser Glu Arg Lys Phe Ser Leu Leu Gln Thr Leu Ala
            180                 185                 190

Thr Phe Arg Gly Gln Tyr Ser Asn Ser Val Phe Ile Arg Leu Tyr Val
        195                 200                 205

Ser Pro Asp Lys Ala Ser Asn Glu His Ile Leu Lys Leu Asp Gln
        210                 215                 220

Ala Thr Leu Ser Leu Ala Val Arg Glu Asp Tyr Leu Asp Asn Ser Thr
225                 230                 235                 240

Glu Ala Lys Ser Tyr Arg Asp Ala Leu Tyr Lys Phe Met Val Asp Thr
                245                 250                 255

Ala Val Leu Leu Gly Ala Asn Ser Ser Arg Ala Glu His Asp Met Lys
            260                 265                 270

Ser Val Leu Arg Leu Glu Ile Lys Ile Ala Glu Ile Met Ile Pro His
        275                 280                 285

Glu Asn Arg Thr Ser Glu Ala Met Tyr Asn Lys Met Asn Ile Ser Glu
290                 295                 300

Leu Ser Ala Met Ile Pro Gln Phe Asp Trp Leu Gly Tyr Ile Lys Lys
305                 310                 315                 320

Val Ile Asp Thr Arg Leu Tyr Pro His Leu Lys Asp Ile Ser Pro Ser
                325                 330                 335

Glu Asn Val Val Val Arg Val Pro Gln Tyr Phe Lys Asp Leu Phe Arg
            340                 345                 350

Ile Leu Gly Ser Glu Arg Lys Lys Thr Ile Ala Asn Tyr Leu Val Trp
        355                 360                 365

Arg Met Val Tyr Ser Arg Ile Pro Asn Leu Ser Arg Arg Phe Gln Tyr
370                 375                 380

Arg Trp Leu Glu Phe Ser Arg Val Ile Gln Gly Thr Thr Thr Leu Leu
385                 390                 395                 400

Pro Gln Trp Asp Lys Cys Val Asn Phe Ile Glu Ser Ala Leu Pro Tyr
                405                 410                 415

Val Val Gly Lys Met Phe Val Asp Val Tyr Phe Gln Glu Asp Lys Lys
            420                 425                 430

Glu Met Met Glu Glu Leu Val Glu Gly Val Arg Trp Ala Phe Ile Asp
        435                 440                 445

Met Leu Glu Lys Glu Asn Glu Trp Met Asp Ala Gly Thr Lys Arg Lys
450                 455                 460

Ala Lys Glu Lys Ala Arg Ala Val Leu Ala Lys Val Gly Tyr Pro Glu
465                 470                 475                 480

Phe Ile Met Asn Asp Thr His Val Asn Glu Asp Leu Lys Ala Ile Lys
                485                 490                 495

Phe Ser Glu Ala Asp Tyr Phe Gly Asn Val Leu Gln Thr Arg Lys Tyr
            500                 505                 510

Leu Ala Gln Ser Asp Phe Phe Trp Leu Arg Lys Ala Val Pro Lys Thr
        515                 520                 525

Glu Trp Phe Thr Asn Pro Thr Thr Val Asn Ala Phe Tyr Ser Ala Ser
530                 535                 540

Thr Asn Gln Ile Arg Phe Pro Ala Gly Glu Leu Gln Lys Pro Phe Phe
545                 550                 555                 560

Trp Gly Thr Glu Tyr Pro Arg Ser Leu Ser Tyr Gly Ala Ile Gly Val

-continued

```
                565                 570                 575
Ile Val Gly His Glu Phe Thr His Gly Phe Asp Asn Asn Gly Arg Lys
            580                 585                 590

Tyr Asp Lys Asn Gly Asn Leu Asp Pro Trp Trp Ser Thr Glu Ser Glu
        595                 600                 605

Glu Lys Phe Lys Glu Lys Thr Lys Cys Met Ile Asn Gln Tyr Ser Asn
    610                 615                 620

Tyr Tyr Trp Lys Lys Ala Gly Leu Asn Val Lys Gly Lys Arg Thr Leu
625                 630                 635                 640

Gly Glu Asn Ile Ala Asp Asn Gly Gly Leu Arg Glu Ala Phe Arg Ala
                645                 650                 655

Tyr Arg Lys Trp Ile Asn Asp Arg Arg Gln Gly Leu Glu Glu Pro Leu
            660                 665                 670

Leu Pro Gly Ile Thr Phe Thr Asn Asn Gln Leu Phe Phe Leu Ser Tyr
        675                 680                 685

Ala His Val Arg Cys Asn Ser Tyr Arg Pro Glu Ala Ala Arg Glu Gln
    690                 695                 700

Val Gln Ile Gly Ala His Ser Pro Pro Gln Phe Arg Val Asn Gly Ala
705                 710                 715                 720

Ile Ser Asn Ser Glu Glu Phe Gln Lys Ala Phe Asn Cys Pro Pro Asn
                725                 730                 735

Ser Thr Met Asn Arg Gly Met Asp Ser Cys Arg Leu Trp
            740                 745
```

<210> SEQ ID NO 2
<211> LENGTH: 20
<212> TYPE: PRT
<213> ORGANISM: Homo sapiens

<400> SEQUENCE: 2

```
Val Gly Gly Thr Leu Val Leu Gly Thr Ile Leu Phe Leu Val Ser Gln
1               5                   10                  15

Gly Leu Leu Ser
            20
```

<210> SEQ ID NO 3
<211> LENGTH: 20
<212> TYPE: PRT
<213> ORGANISM: Artificial Sequence
<220> FEATURE:
<223> OTHER INFORMATION: Description of Artificial Sequence: Human PHEX derivative

<400> SEQUENCE: 3

```
Val Leu Thr Val Ile Ala Gln Gln Thr Thr Leu Phe Leu Val Ser Gln
1               5                   10                  15

Gly Leu Leu Ser
            20
```

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence: Human PHEX derivative

<400> SEQUENCE: 4

```
Val Leu Thr Val Ile Ala Gln Gln Thr Thr Ser Gln Gly Leu Leu Ser
1               5                   10                  15
```

```
<210> SEQ ID NO 5
<211> LENGTH: 52
<212> TYPE: DNA
<213> ORGANISM: Artificial Sequence
<220> FEATURE:
<223> OTHER INFORMATION: Description of Artificial Sequence: Primer

<400> SEQUENCE: 5
ctgacagtga tcgctcaaca aacaaccagt caaggtctct taagtctcca ag            52

<210> SEQ ID NO 6
<211> LENGTH: 51
<212> TYPE: DNA
<213> ORGANISM: Artificial Sequence
<220> FEATURE:
<223> OTHER INFORMATION: Description of Artificial Sequence: Primer

<400> SEQUENCE: 6
ggttgtttgt tgagcgatca ctgtcaggac aaacacgacc agggcaattc g             51
```

COMPOSITION, METHODS AND REAGENTS FOR THE SYNTHESIS OF A SOLUBLE FORM OF HUMAN PHEX

BACKGROUND OF THE INVENTION

The PHEX gene (formerly PEX; Phosphate regulating gene with homologies to Endopeptidases on the X chromosome) was identified by a positional cloning approach as the candidate gene for X-linked hypophosphatemia (XLH) (Francis et al., 1995). XLH is a Mendelian disorder of phosphate homeostasis characterized by growth retardation, rachitic and osteomalacic bone disease, hypophosphatemia, and renal defects in phosphate re-absorption and vitamin D metabolism (Rasmussen and Tenenhouse, 1995). Using the information made available by the publication of the sequence of the PHEX gene, and standard techniques obvious to those skilled in the art, several groups have cloned and sequenced the human and mouse PHEX/Phex cDNAs (Du et al., 1996; Lipman et al., 1998; Grieff et al., 1997; Beck et al., 1997; Guo and Quarles, 1997; Strom et al., 1997) (PHEX/Phex refers to the human and mouse genes, respectively). Amino acid sequence comparisons have demonstrated homologies between PHEX/Phex protein and members of the neutral endopeptidase family as previously observed in the partial sequence of the candidate gene (Francis et al., 1995). The peptidases of the neutral endopeptidase family are zinc-containing type II integral membrane glycoproteins with a relatively short cytoplasmic N-terminal region, a single transmembrane domain, and a long extracytoplasmic domain, which contains the active site of the enzyme (Devault et al., 1987).

The mechanism by which loss of PHEX function elicits the bone and renal abnormalities observed in XLH patients is not clear. There are no data suggesting the presence of PHEX/Phex mRNA in the kidney (Du et al., 1996; Beck et al., 1997; Grieff et al., 1997). The increased renal phosphate excretion in Hyp mice is due to a down-regulation of the phosphate transporter, which is necessary for the re-absorption of the phosphate from the nephron (Tenenhouse 1998). The serum concentration of $1,25(OH)_2D3$ (calcitriol) was found to be the same in Hyp mice as in normal littermates (Meyer 1980). However, the Hyp kidney showed an accelerated degradation of the vitamin D metabolite to $1,24,25(OH)_3D3$, a metabolite with reduced activities (Tenenhouse 1988). In the presence of a phosphate rich diet, Hyp mice experienced an increase in serum $1,25(OH)_2D3$ and a fall in the C-24 oxidation products, while normal mice experienced no such changes (Tenenhouse 1990). To summarize, the renal disorder in vitamin D metabolism in Hyp mice appears to be secondary to the phosphate disorder.

PHEX/Phex mRNA was detected in bones by Northern blot hybridization and in other adult and fetal tissues such as lungs, liver, muscles, and ovaries by RT-PCR and RNase protection assays (Du et al., 1996; Beck et al., 1997). In situ hybridization performed on sections of embryos and newborn mice showed the presence of Phex mRNA in osteoblasts and odontoblasts (Ruchon et al., 1998). Phex gene expression was detectable on day 15 of embryonic development, which coincides with the beginning of intracellular matrix deposition in bones. Moreover, Northern analysis of total RNA from calvariae and teeth of 3-day-old and adult mice showed that the abundance of the Phex transcript is decreased in adult bones and in non growing teeth. This result was confirmed when the presence of the Phex protein in newborn adult bones was investigated by Western blotting using a monoclonal antibody raised against the human PHEX. Immunohistochemical studies on a 2 month-old mouse showed exclusive labelling of mature osteoblasts and osteocytes in bones and of odontoblasts in teeth (Ruchon et al., 2000: J Bone Miner. Res. In press). Taken together these results suggest that PHEX/Phex plays an important role in the development and maintenance of mineralization in these tissues.

Further insights into the role of PHEX in bone metabolism were provided by experimental studies on cases of oncogenic osteomalacia (OOM), a tumor-associated sporadic condition with very similar clinical indications. There is strong evidence that a tumor-produced humoral factor inhibits renal phosphate re-absorption and vitamin D synthesis resulting in osteomalacia (Nelson et al., 1997). Experimental studies on Hyp and Gy mice, the murine model of human XL, also suggest the involvement of a humoral factor. In both mouse models, mutations have been identified in the Phex gene, which also appear to result in loss of function of the gene product (Strom et al., 1997; Beck et al., 1997).

Considering the similarities between PHEX protein and the other members of the metallopeptidase family of enzymes, it has been speculated that PHEX metabolizes a peptide hormone that modulates renal tubular phosphate re-absorption. Such an activity could involve either the processing of a phosphate reabsorbing hormone precursor to its active form or the inactivation of a circulating phosphaturic factor. There is evidence of intrinsic abnormalities in osteoblasts from Hyp mice (Ecarot et al., 1992). A defective phosphate transport was also observed in osteoblasts from Hyp mice (Rifas et al., 1994). PHEX might thus be involved in the control of bone metabolism both indirectly at the level of the kidney by controlling renal phosphate reabsorption and directly at the level of bones by inactivating a trophic peptide factor controlling either osteoblast or osteoclast functions or both.

Since absence of a functioning PHEX gene leads to hypophosphatemia, it should be possible to control human diseases involving hyperphosphatemia through the inhibition of this enzyme. Thus, inhibiting PHEX will cause a reduction in blood phosphate concentration, allowing for the prevention and reduction of hyperphosphatemiarelated disorders in humans and animals. Reduced renal excretion of phosphorus due to impaired kidney functions is the most common cause of hyperphosphatemia. In the specific case of secondary hyperparathyroidism (renal osteodystrophy), proper phosphate concentration would also benefit the patient by leading to an increase in endogenous calcitriol production and/or a lowering of PTH level. Therefore the early and adequate inhibition of PHEX activity could mitigate the serious consequences of renal osteodystrophy, giving patients an opportunity for an improved quality of life without the pain and mobility problems of advanced renal osteodystrophy. Hyperphosphatemia is defined in adults as an elevation of serum phosphorus above 1.67 mmol/L (5 mg/dL). Hyperphosphatemia is a common finding with many causes (Harrison's $14^{Th}$ Ed CD-ROM, McGraw Hill Health Professions Division, New York N.Y., chapter 356).

Hyperparathyroidism or renal osteodystrophy results from the progressive nature of chronic renal failure. The leading causes of chronic renal failure are diabetes (43%), hypertension (35%) and glomerulonephritis (14%) among US Medicare patients (patients over 65 years of age). (Harrison's $14^{Th}$ Ed CD-ROM, McGraw Hill Health Professions Division, New York N.Y., chapter 271, FIG. 271.1).

Hyperphosphatemia is potentially dangerous because of metastatic calcification. Although only an approximate guide, a calcium-phosphorus product [serum Ca (mg/dL) X serum P (mg/dL)] greater than 70 indicates a potential threat of calcification. Patients with this disease suffer from bone and joint pain, osteopenia, deformities, fractures, muscle weakness and extra-skeletal calcification.

Irrespective of the underlying cause, the disease is characterized by a progressive loss of the kidney ability to eliminate waste, to produce calcitriol ($1,25(OH)_2D3$) and to excrete phosphate. Increased phosphate excretion is achieved with elevated PTH.

The direct effect of phosphate on PTH levels is well documented. In the presence of increasing phosphate concentration, intact fresh parathyroid gland showed increased PTH secretion (Almaden, 1996). A high phosphate diet causes elevated PTH while maintaining normal serum phosphate; in contrast, parathyroidectomized rats fed the same diet showed elevated phosphate levels (Borle, 1981 and Demeter 1991). Results in patients with mild to moderate renal failure showed that phosphate concentration correlated directly with PTH (Kates, 1997).

Although the treatment of disorders involving an inappropriate expression of PHEX is a primary goal of the present invention, the opposite is under the scope thereof. Compositions comprising a soluble active PHEX or a nucleic acid encoding same for the treatment of disorders involving PHEX deficiencies is an object of this invention.

The zinc metallopeptidase family (also known as the Zincins; see Hooper FEBS Letters 354, 1–6, 1994) is characterized by the presence of a zinc atom at the active site. This large family consists of several sub-classes that can be distinguished by their active site structure. One such sub-family is the gluzincins, which is characterized by the HEXXH motif and a glutamic acid as the third zinc ligand. This sub-family includes thermolysin, ACE (angiotensin converting enzyme), aminopeptidases and enzymes of the Neutral Endopeptidase or Neprilysin (NEP) family. NEP itself is now considered the prototype for the enzymes of the family (Crine 1997). These peptidases share extensive sequence and structural similarities. In addition to NEP, there are five other NEP-like enzymes in the public domain: the endothelin-converting enzymes ECE-1, ECE-2, Kell, XCE and PHEX (for a review, see: Turner and Tanzawa, 1997b). Several family members can cleave the same peptide substrates and the same inhibitor can inhibit more than one NEP-like enzyme. In fact, several chemical entities are capable of inhibition of more than one enzyme of the gluzincin sub-family (Roques B. P. Path Biol 1998 46,3, 191-200). Therefore, known gluzincins inhibitors can be assayed in a PHEX enzymatic assay and identified as a PHEX inhibitor. Among the methods of this invention is the administration of "PHEX inhibitors". As referred to herein, the term "PHEX inhibitor" includes any compound that inhibits the enzymatic action of PHEX.

SUMMARY OF THE INVENTION

Towards this objective, we have prepared various reagents and tools designed to produce recombinant forms of PHEX and to purify both the recombinant and native enzymes from cell fractions, spent culture media and tissue extracts. We have cloned a CDNA encoding the full-length human PHEX protein into various expression vectors. These PHEX-encoding vectors were introduced by transfection into various cell lines including COS-1 (monkey kidney) cells, CHO (Chinese Hamster Ovary) cells, and LLC-PK1 (porcine kidney) cells. Permanent cell lines were established and shown to stably express the PHEX protein at the cell surface. A procedure was established to rapidly prepare a membrane fraction enriched in the recombinant PHEX protein.

PHEX is an intrinsic membrane protein anchored by a hydrophobic 20 amino acid sequence located near the N-terminus. The purification of an intrinsic membrane-bound protein requires the use of detergents to free it from the lipidic environment of the membrane. These detergents can interfere with the catalytic activity of the enzyme. Moreover, the detergent-purified proteins usually present stability and solubility problems, especially if concentrated solutions and/or large amounts of the protein are needed, such as those required for crystallization and high throughput screening assays. To facilitate the preparation and purification in high yields of a fully active enzyme, it is thus preferable to work with a soluble form of PHEX. Soluble forms of NEP (Lemay et al., 1989) and ECE (Korth et al., 1997) consisting of the entire ectodomain but lacking the cytosolic and hydrophobic transmembrane domains have been constructed and shown to possess enzymatic activities identical to those of the native membrane-bound homolog. A soluble form of recombinant PHEX was thus constructed by modification of the signal peptide/transmembrane region of the protein. The soluble PHEX comprises PHEX ectodomain or a catalytic part thereof; this soluble form of PHEX is referred to as secPHEX. The expression vector encoding secPHEX was transfected into LLC-PK1 cells and a permanent cell line expressing the chimeric PHEX protein on a stable basis was established. Analysis of the spent medium of this cell line by Western blot was shown to contain high levels of a secPHEX. This secPHEX was purified using either immunoaffinity or ion exchange chromatography. Ion-exchange chromatography was found to be the most efficient method to purify secPHEX from spent culture medium. The purified secPHEX was shown to be active in an enzymatic assay using PTHrP107-139 as a substrate. Moreover, the availability of this secPHEX rendered possible its use as an antigen for the production of anti-PHEX antibodies.

Monoclonal antibodies specific for PHEX were generated by immunizing mice with a PHEX-derived recombinant fusion protein produced in *E. coli*. These monoclonal antibodies were used to purify recombinant PHEX by various immunoaffinity procedures. PHEX-specific monoclonal antibodies also proved useful for characterizing PHEX expression in bone by immunohistochemical techniques and Western blotting.

The present invention also relates to compositions for treating PHEX-related disorders in humans and animals. The present invention particularly provides compositions for the treatment of hyperphosphatemia, including its most frequent manifestations, secondary hyperparathyroidism and renal osteodystrophy. The compositions comprise an anti-PHEX molecule which, by inhibiting PHEX activity, induce an increase in phosphate excretion as well as a reduction in gut phosphate absorption, thus reducing and/or preferably preventing hyperphosphatemia and the appearance of its most frequent consequences, secondary hyperparathyroidism and renal osteodystrophy. For example, with such a treatment, normophosphatemia is maintained in patients with mild kidney failure at the expense of PHEX activity as opposed to an increase in PTH serum concentration. While the phenotype resulting from PHEX mutation suggests that PHEX inhibition may be toxic, an attentive study of the physiology suggests otherwise. The dominant nature of the phosphate excretion suggests that only partial inhibition may be required to achieve the desired result.

Observations in heterozygous females indicate that an inhibition of much less than 50% is required. At this low level of inhibition, the other features of XLH that are gene-dosage-dependent or phosphate-dependent may not be significant.

Accordingly, a first object of this invention is to provide compositions comprising PHEX enzyme or mutants, or anti-PHEX ligands. These compositions are particularly useful for treating PHEX-related disorders in humans and animals. Further objects include the provision of the following: (1) diagnostic kits for detecting the presence or amount of PHEX in a sample; (2) a method for detecting the presence or amount of PHEX in a sample; (3) devices for purifying PHEX or mutants thereof; (4) devices for screening PHEX ligands; (5) a method for obtaining a PHEX ligand; and (6) enzymatic assays involving PHEX and a PHEX substrate.

DESCRIPTION OF THE SPECIFIC EMBODIMENTS OF THE INVENTION

BRIEF DESCRIPTION OF THE FIGURES

This invention will now be described with reference to the following specific embodiments and drawings, which purpose is to illustrate the invention and not to limit its scope.

FIG. 1: Construction of a soluble form of PHEX. FIG. 1A (construct 1) represents the schematic structure of the native membrane-bound form of the enzyme and the construct in which the POMC signal peptide has been fused in frame with the ectodomain of the native enzyme (construct 2). FIG. 1B represents the construct where part of the sequence for the hydrophobic transmembrane domain in construct 1 (SEQ ID NO: 2) (underlined) has been replaced by the more hydrophilic domain in construct 2 (SEQ ID NO: 3). In construct 3 (SEQ ID NO: 4), part of the hydrophobic sequence has been deleted in addition to insertion of the hydrophilic sequence as in construct 2 (SEQ ID NO: 3).

FIG. 2: Amino acid sequence of human PHEX (SEQ ID NO: 1). The boxed sequence represents the hydrophobic signal peptide/transmembrane domain. The underlined sequence represents the segment used for making the E. coli GST-fusion protein for monoclonal antibody production.

FIG. 3: Screening of PHEX monoclonal antibodies. Monoclonal antibodies were first selected for their capacity to bind the $PHEX_{121-294}$ fragment produced in E. coli as tested by using the spent medium of hybridoma cultures in ELISA assays. Immunoglobulins from positive cultures were next tested for their ability to bind membrane-bound PHEX from LLC-PK1 cells transfected with the PHEX expression vector.

FIG. 5: Ion-exchange chromatography purification of secPHEX. Concentrated spent culture medium from secPHEX expressing LLC-PK1 cells was loaded on SP-Sepharose column and the proteins eluted with a linear NaCl gradient. Fractions were analysed on a 7.5% SDS polyacrylamide gel and detected by immunoblotting (FIG. 5A) or by silver staining (FIG. 5B).

Figure 3A:
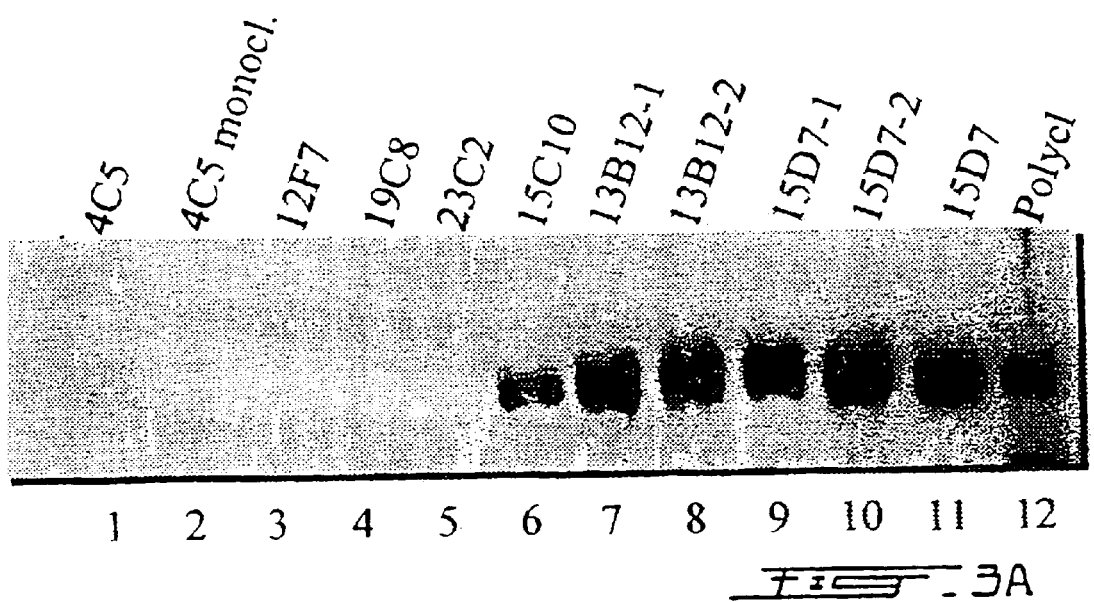
FIG. 3A is the Western blot analysis of LLC-PK1 extracts stained with the various hybridoma supernatants. Track 12 is the staining pattern obtained with PHEX polyclonal antibody prepared in rabbit.

In order to provide a clear and consistent understanding of terms used in the present description, a number of definitions are provided hereinbelow. Unless defined otherwise, the scientific and technological terms and nomenclature used herein have the same meaning as commonly understood by a person of ordinary skill to which the present invention pertains.

As used herein, the designation "variant" denotes, in the context of a sequence whether a nucleic acid or amino acid sequence, a molecule that retains a biological activity (either functional or structural) that is substantially similar to that of the original sequence. This variant or equivalent may be a natural intra-species or inter-species variant or may be prepared synthetically. Such variants include amino acid sequences having substitutions, deletions or additions of one or more amino acids, provided that the biological activity of the protein is conserved. The same applies to derivatives of nucleic acid sequences which can have substitutions, deletions or additions of one or more nucleotides, provided that the biological activity of the sequence is generally maintained. When relating to a protein sequence, the substituting amino acid generally has chemico-physical properties which are similar to that of the substituted amino acid. The similar chemico-physical properties include similarities in charge, bulkiness, hydrophobicity, hydrophilicity and the like. The term "variants" is intended to include "fragments", "segments", "functional derivatives", "analogs" or "chemical derivatives" of the subject matter of the present invention.

The term "hydrophobic amino acid residue" is intended to mean an amino acid chosen from the following group: alanine, valine, leucine, isoleucine, proline, methionine, phenylalanine, tryptophan or variants thereof (A. L. Lehninger, Principles of Biochemistry (Worth Publishers, Inc.: 1982), at p.101). In the context of this invention, aliphatic amino acids are preferred.

The expression "anti-PHEX" molecule is intended to mean a molecule such as an "antisense nucleic acid molecule", an "antibody", an "inhibitor" or an "antagonist" (i.e., any molecule capable of hindering PHEX activity).

The present invention also provides antisense nucleic acid molecules which can be used for example to decrease or abrogate the expression of the nucleic acid sequences or proteins of the present invention. An antisense nucleic acid molecule according to the present invention refers to a molecule capable of forming a stable duplex or triplex with a portion of its targeted nucleic acid sequence (DNA or RNA). The use of antisense nucleic acid molecules and the design and modification of such molecules is well known in the art as described for example in WO 96/32966, WO 96/11266, WO 94/15646, WO 93108845 and U.S. Pat. No. 5,593,974. Antisense nucleic acid molecules according to the present invention can be derived from the nucleic acid sequences and modified in accordance to well known methods. For example, some antisense molecules can be designed to be more resistant to degradation to increase their affinity to their targeted sequence, to affect their transport to chosen cell types or cell compartments, and/or to enhance their lipid solubility bu using nucleotide analogs and/or substituting chosen chemical fragments thereof, as commonly known in the art.

In general, techniques for preparing antibodies (including monoclonal antibodies and hybridomas) and for detecting antigens using antibodies are well known in the art (Campbell, 1984, In "Monoclonal Antibody Technology: Laboratory Techniques in Biochemistry and Molecular Biology", Elsevier Science Publisher, Amsterdam, The Netherlands) and in Harlow et al., 1988 (in: Antibody-A Laboratory Manual, CSH Laboratories). The present invention also provides polyclonal, monoclonal antibodies, or humanized versions thereof, chimeric antibodies and the like which inhibit or neutralize their respective interaction domains and/or are specific thereto.

As commonly known, a "mutation" is a detectable change in the genetic material which can be transmitted to a daughter cell. As well known, a mutation can be, for example, a detectable change in one or more deoxyribonucleotide. For example, nucleotides can be added, deleted, substituted for, inverted, or transposed to a new position. Spontaneous mutations and experimentally induced mutations exist. The result of a mutations of nucleic acid molecule is a mutant nucleic acid molecule. A mutant polypeptide can be encoded from this mutant nucleic acid molecule. A mutation may result in an unaffected mutant, a negatively or positively partially affected mutant, or an inactive mutant. In the embodiment of the present invention, a mutant has been obtained which has the particular capacity to bind to a PHEX but has an inactive catalytic site.

As used herein, the term "purified" refers to a molecule having been separated from a cellular component. Thus, for example, a "purified protein" has been purified to a level not found in nature. A "substantially pure" molecule is a molecule that is lacking in most other cellular components.

As used herein, the terms "molecule" or "ligand" are used interchangeably and broadly to refer to natural, synthetic or semi-synthetic molecules or compounds. The term "molecule" therefore denotes for example chemicals, macromolecules, micromolecules, cell or tissue extracts (from plants or animals) and the like. Non limiting examples of molecules include nucleic acid molecules, peptides, antibodies, carbohydrates and pharmaceutical agents. The agents can be selected and screened by a variety of means including random screening, rational selection and by rational design using for example protein or ligand modelling methods such as computer modelling. The terms "rationally selected" or "rationally designed" are meant to define compounds which have been chosen based on the configuration of interacting domains of the present invention. As will be understood by the person of ordinary skill, macromolecules having non-naturally occurring modifications are also within the scope of the term "molecule". The distinction between a "macro" and a "micro" molecule is made on the basis of size. For example, an oligonucleotide and a peptide having no more than about 100 nucleotides or amino acids. respectively, would be considered micromolecules, whereas a gene, a complete cDNA and a protein would generally be classified as macromolecules because of their larger size. The molecules identified in accordance with the teachings of the present invention have a therapeutic value in diseases or conditions in which the physiology or homeostasis of the cell and/or tissue is compromised by a defect in the nature or level of PHEX gene product. They may also have diagnostic value in the evaluation of the same diseases or conditions.

METHODS

Production of Monoclonal Antibodies

The cDNA corresponding to amino acids 121 to 294 of the PHEX amino acid sequence (underlined segment in FIG. 2) was used to construct a GST-fusion protein in *E. coli*. This fusion protein was purified from *E. coli* extracts by affinity chromatography on a glutathione-Sepharose column. After thrombin cleavage, the PHEX portion of the GST fusion protein was further purified by electro-elution from a polyacrylamide gel. This material was used to immunize 4 mice (5 injections of ≈50 µg of PHEX$_{121-294}$). Blood was collected from each mouse after the immunization schedule and the presence of antibodies in mice serum was assessed by ELISA using microtiter plates coated with PHEX$_{121-294}$ from *E. coli* extracts. Mice sera were also tested for the presence of PHEX antibodies by Western blotting extracts of LLC-PK1 cells transfected with the PHEX expression vector. Out of the 4 mice immunized, 3 showed good results both in ELISA and Western blots. One mouse selected for its high titer of PHEX-specific antibodies (as measured by ELISA) was sacrificed and its spleen cells were collected and immortalized by fusion with myeloma cells (strain). Hybridoma cells were selected for their ability to grow in HAT selection medium and cloned by several rounds of limiting dilution.

Expression of Human PHEX in Transfected Cells

A cDNA encoding for the full-length human PHEX was obtained by Polymerase Chain Reaction (PCR) as previously described (Beck et al., 1997). The plasmid pCR2.1-PHEX-FLB was generated by cloning this cDNA into pCR2.1 (Invitrogen). A restriction fragment (Spel-EcoRV), which contained the entire PHEX coding sequence, was digested, blunted, and subcloned into the mammalian expression vector (pCDNA3/RSV). The resulting plasmid (pCDNA3/RSV-PHEX-FLB) contained the entire PHEX cDNA under the control of the Rous Sarcoma Virus (RSV) promoter.

This recombinant vector was then expressed transiently in COS-1 cells by transfection. COS-1 cells were grown at 37° C. under a 5% $CO_2$ atmosphere in Dulbecco's modified Eagle's medium (DMEM) containing 5% COSMIC (Hiclone), 100 U/ml penicillin, and 100 µg/ml streptomycin. COS-1 cells were transfected using the calcium phosphate-DNA co-precipitation procedure. The day following transfection, the serum-containing medium was changed for a synthetic medium that consists of DMEM supplemented with 2.5 µg/ml insulin, 17.5 µg/ml transferrin, 2 µg/ml ethanolamine, 100 µg/ml soybean trypsin inhibitor and 10 µg/ml aprotinin. Finally, sodium butyrate was added to the synthetic medium at a concentration of 10 mM to enhance the expression of the plasmids carrying the RSV promoter. After 48 h, the cells were harvested and the membranes were prepared according to the procedure of Korth et al. (1997).

The plasmid pCDNA3/RSV-PHEX-FLB was also transfected in LLC-PK1 cells by the $CaPO_4$ precipitation method. Transfected cells were selected by adding 400 µg/ml of G-418 to the culture medium. G-418 resistant cells were grown in 150 mm dishes containing 20 ml medium 199 with Earle's salts, 2 mM L-glutamine, Hepes and bicarbonate buffer supplemented with 5% fetal bovine serum (FBS), 50 units/ml penicillin, and 50 µg/ml streptomycin. Cells were grown up to confluence for about a week and harvested by scraping with a rubber policeman.

Construction and Expression of a Soluble Form of Recombinant PHEX

To obtain a soluble form of recombinant human PHEX, we first attempted to fuse in frame the CDNA encoding the signal sequence of a secreted protein (pro-opiomelanocortin or POMC) to the cDNA sequence of the ectodomain of human PHEX (FIG. 1, panel A). This strategy, which had successfully been used for other members of this family of peptidases, namely NEP and ECE (Lemay et al., 1989; Korth et al., 1997), resulted in the production of a misfolded PHEX protein that remained trapped in the rough endoplasmic of transfected cells. Consequently, an alternate strategy was developed consisting in the substitution of selected amino acids in the N-terminal hydrophobic membrane anchor of PHEX to transform it into a cleavable signal sequence.

Transformation of the membrane anchor into a cleavable signal sequence was carried out on the pCDNA3/RSV/PHEX-FLB plasmid. Site-directed mutations (9 codons) and deletions (4 codons) were introduced by Polymerase Chain Reaction (PCR) amplification using oligonucleotide #5136 as the sense primer 5'CTGACAGTGATCGCTCAACAAA-CAACCAGTCAAGGTCTCTTAAGTCTCCAAG 3' and oligonucleotide #5134 as the antisense primer 5'GGT-TGTTTGTTGAGCGATCACTGTCAGGA-CAAACACGACCAGGGCAATTCG 3' (FIG. 1, panel B). The resulting plasmid, designated as to pCDNA3/RSV/PHEX-MutE, encoded for a secreted form of PHEX (secPHEX).

This recombinant vector was then expressed transiently in COS-1 cells by transfection as described above. After 16 hours of incubation, the medium was recovered and concentrated by ultrafiltration (MW cut-off=30 kDa) using a Centriprep cartridge (Amicon). To induce the stable expression of secPHEX in LLC-PK, cells, the plasmid pCDNA3/RSV-PHEX-MutE was transfected in LLC-PK, cells by the $CaPO_4$ precipitation method. Transfected cells were selected by adding 400 µg/ml G418 to the medium. G418 resistant cells were grown in 150 mm dishes containing 20 ml of medium 199 with Earle's salts, 2 mM L-glutamine, 1 mM sodium pyruvate, Hepes and bicarbonate buffer supplemented with 5% fetal bovine serum (FBS), 100 µg/ml G-418, 50 units/ml penicillin, and 50 µg/ml streptomycin. Cells were grown up to confluence, for about a week. To produce secPHEX, confluent cells were incubated for 4 days in synthetic medium that consists of 199 medium supplemented with 2.5 µg/ml insulin, 17.5 µg/ml transferrin, 2 µg/ml ethanolamine, 100 µg/ml soybean trypsin inhibitor and 10 µg/ml aprotinin. Finally, sodium butyrate was added to the synthetic medium, at a concentration of 10 mM, to enhance the expression of the secPHEX gene, which is under the control of the RSV promoter. After 4 days, the medium was recovered, centrifuged and concentrated by cross-flow filtration (MW cut-off=30 kDa) using a Sartocon Micro Unit (Sartorius). Typically, 600 ml of crude spent medium from secPHEX-transfected LLC-PK1 cells are concentrated to 30 ml before loading on ion-exchange column for purification.

Characterization of secPHEX was done by immunoblotting. Briefly, proteins from the concentrated media were resolved on 7.5% SDS-PAGE, and transferred onto 0.45 µm nitrocellulose membranes. Membranes were incubated for one hour in TTBS (Tris Buffered Saline containing 0.05% Tween-20) supplemented with 5% (w/v) instant non-fat dry milk (Carnation). Membranes were washed rapidly with TTBS and incubated with a 1:200 dilution of the anti-(human PHEX) monoclonal antibody (13B12) in TTBS supplemented with 1% BSA (w/v). Membranes were washed in TTBS and incubated for one hour with a HRP-labeled second antibody in TTBS supplemented with 1% BSA (w/v). Membranes were washed and processed using a chemiluminescence reagent (NEN).

Other signal peptide coding sequences may be used in so far as they properly govern the secretion of PHEX in the extracellular space (the culture medium or a secretion fluid, depending on the host cell, tissue or organism used).

Immunoprecipitation Assay

The immunoprecipitation assay was performed by first saturating protein A-Sepharose beads (Pharmacia) with a rabbit antimouse IgG fraction and then with the mouse immunoglobulins from hybridoma supernatants. After washing in PBS, these beads were incubated in aliquots of the spent medium of LLC-PK1 cells producing secPHEX (40 µg of total protein) diluted in immunoprecipitation (IPP) buffer (20 mM Tris-HCl pH7.4, 100 mM NaCl, 2% sodium deoxychol ate, 2% Triton X-100, 0.2% SDS, and 0.2% BSA). The beads were pelleted by centrifugation, washed twice in IPP buffer and once in PBS and the presence of secPHEX bound to the immunoaffinity support was assessed by submitting the proteins bound to proteins A Sepharose in a non-covalent fashion to boiling in the electrophoresis sample buffer before immunoblot analysis.

Purification of the Soluble Form of PHEX

1) Purification of secPHEX by Ion-exchange Chromatography

The concentrated medium was loaded on a SP-Sepharose cation-exchange column (Pharmacia) previously equilibrated with 50 mM sodium phosphate pH 6.6 containing 50 mM NaCl The column was washed with 10 column volumes of the same buffer and SecPHEX was eluted with a 50 mM to 1M NaCl gradient. Fractions were analyzed by SDS-PAGE and immunoblotting, as described above, and fractions containing secPHEX visualized by silver staining.

2) Purification of secPHEX by Immunoaffinity Chromatography

An immunoaffinity column was built by linking antibody 4C5 to Affigel (BioRad). Immunoglobulins were purified from 4C5 ascite on protein G column (Amersham-Pharmacia) and coupled to the Affigel matrix as recommended by the supplier (BioRad). Two mg of IgG were attached to the matrix in a 4 ml column. The column was washed as recommended by the supplier and equilibrated in 20 mM Tris-HCl pH 8.0. An aliquot of 15 ml of concentrated LLC-PK1 culture medium was circulated overnight on the column. The column was washed with 5 volumes of equilibration buffer. The proteins were eluted with 0.1M triethylamine pH 11.5 and immediately neutralized by the addition of 0.2 volume of 1M phosphate buffer pH 6.8. Proteins in fractions were analyzed by SDS-PAGE and immunoblotting.

Preparation of PHEX-containing Brush Border Membranes

The LLC-PK1 cell line forms polarized epithelial monolayers in culture. Brush border (apical) membranes BBMs were purified from LLC-PK1 cell homogenates as described previously (Blais et al., 1987). Briefly, cell membranes were disrupted by sonication. Non-apical membranes were precipitated at 4° C. by adding $CaCl_2$ to a final concentration of 13 mM under constant agitation. BBMs were fractionated by sequential centrifugation at 950×g for 10 min and then at 35,000×g for 30 min. The final pellet containing BBMs was washed twice with 50 mM Tris-HCl, pH 7.5, and resuspended in the same buffer. The presence of PHEX in BBMs was verified by immunoblotting.

Assay for the Activity of PHEX

An aliquot of purified PHEX containing 2 µg of protein was incubated for 15 min at 37° C. in a volume of 200 µl of 50 mM MES (2-(N-Morpholinoethanesulfonic acid, pH 6.5, containing 150 mM NaCl and 10 µg of PTHrP107-139 as a substrate. After the incubation period, the hydrolysis was stopped by the addition of trifluoroacetic acid to a final concentration of 0.1%. Identification of peptide products was performed by reverse phase high performance liquid chromatography (RP-HPLC) on a C18µBondapak analytical column (Waters) with a UV detector set at 214 nm. Peptides were resolved with a linear gradient of 5% B to 85% B in 45 min at the flow rate of 0.4 ml/min [mobile phase A=0.1% trifluoroacetic acid; mobile phase B=80% acetonitrile ($CH_3CN$), 0.1% trifluoroacetic acid].

RESULTS

Production of Monoclonal Antibodies

Figure 3B:
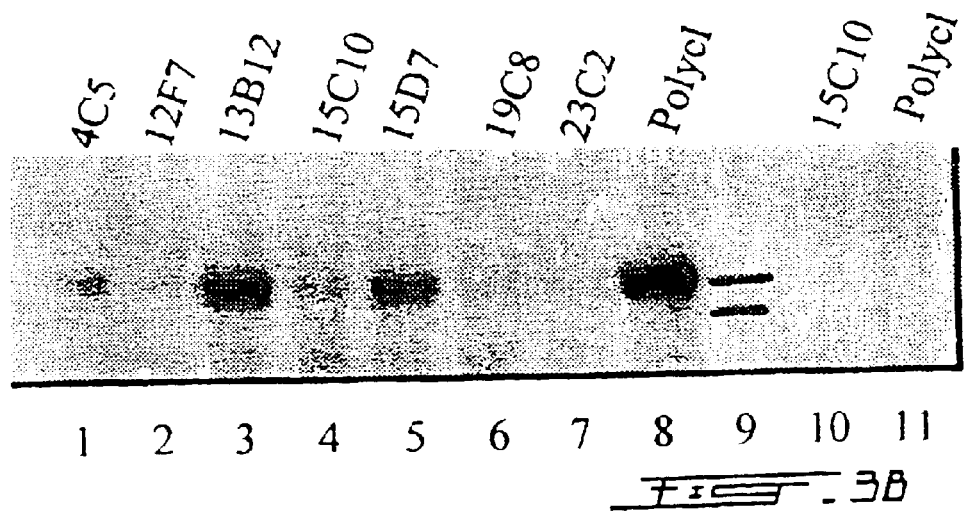
FIG. 3B: immunoprecipitation of a soluble form of PHEX (secPHEX). LLC-PK1 cells were first transfected with a vector encoding a soluble form of PHEX as explained in the Material and Methods section. The spent medium of transfected LLC-PK1 cells was then used as a source of secPHEX for immunoprecipitation experiments. The immunoprecipitation was performed by first saturating protein A-Sepharose beads (Pharmacia) with a rabbit anti-mouse IgG fraction and then with the mouse immunoglobulins from the hybridoma supernatants selected as shown in FIG. 3A. After washing, these beads were incubated in aliquots of the spent medium of LLC-PK1 cells producing secPHEX (40 µg of total protein). The beads were pelleted by centrifugation, washed and the presence of secPHEX was assessed by boiling the proteins bound to protein A-Sepharose in the electrophoresis sample buffer followed by Western blot analysis with a PHEX polyclonal antibody. Track 8 shows the results of an immunoprecipitation done in the same conditions with a rabbit PHEX polyclonal antiserum. Tracks 10 and 11 are control experiments prepared from mock transfected cells.

Throughout the limiting dilution process, hybridoma were tested for their ability to bind to $PHEX_{121-294}$ in the ELISA assay, to recognize recombinant full length PHEX in Western blotting assays (FIG. 3A) and to immunoprecipitate secPHEX (FIG. 3B). Antibody 15D7 showed good results in immunoprecipitation, immunoblotting and also in immunofluorescence experiments (results not shown) and was selected to monitor the expression of PHEX or secPHEX in cultured transfected cells or PHEX in tissues. Other segments of PHEX may be used as antigens provided that they are specific to PHEX in so far as the production of PHEX-specific antibodies is sought.

Expression of Membrane-bound Recombinant PHEX in COS-1 Cells

Figures 4A, 4B:
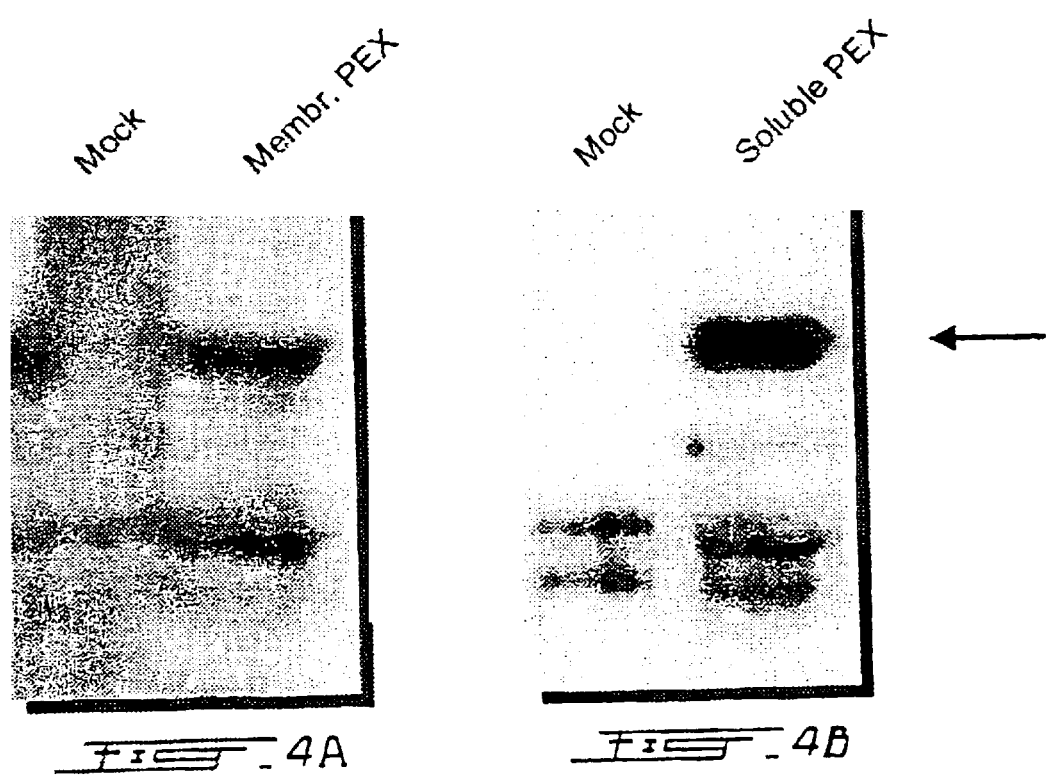
FIG. 4: Expression of membrane-bound and soluble forms of recombinant PHEX in COS-1 cells. COS-1 cells were transfected with expression vectors containing either the entire coding sequence of PHEX (left panel) or a construct capable of promoting the secretion of the PHEX ectodomain (see Methods) (right panel). The cells were kept in culture for 16 h after transfection and either a membrane fraction (left panel) or the spent medium (right panel) was prepared as explained in Methods. The expression of PHEX was monitored in Western blots with monoclonal antibody 15D7. As seen in left panel, a band migrating with a mobility corresponding to an apparent Mr of 105,000 was present in the membrane fraction of cells transfected with the pCDNA3/RSV-PHEX-FLB vector (lane 2). This band was absent from the extract of control cells (lane 1). The right panel shows the presence of a secreted soluble form of PHEX in the spent medium of transfected cells, but not in control mock transfected cells.
Figure 6C:
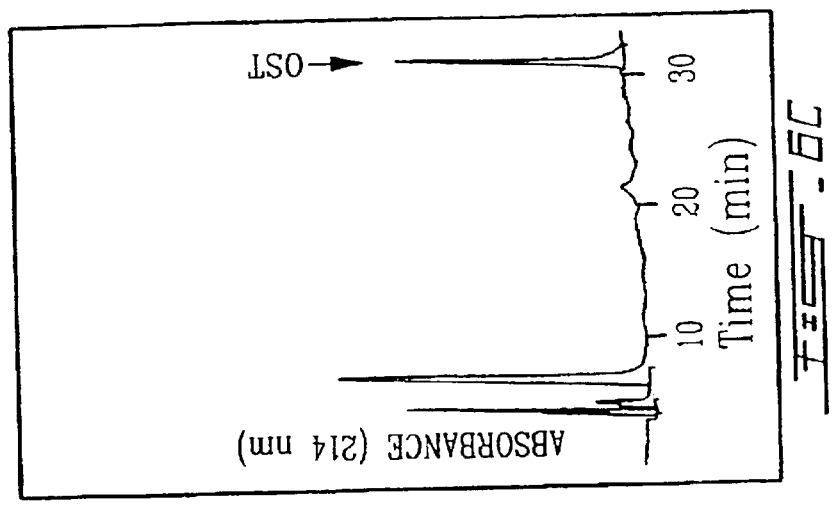
FIG. 6: Enzymatic assay for secPHEX. Purified secPHEX (2 µg) was incubated in the presence of 10 µg PTHrP107-139 and the reaction mixture analyzed by RP-HPLC.
FIG. 6A shows the chromatogram obtained when PTHrP107-139 is incubated in the absence of secPHEX.
FIG. 6B shows the digestion of PTHrP107-139 by secPHEX. This degradation can be totally inhibited by the addition of 0.001M EDTA to the reaction mixture (FIG. 6C). Cleavage of PTHrP107-139 by secPHEX is sensitive to phosphate concentration (FIGS. 6D to 6H: 1, 5, 10, 25, 50 mM phosphate, respectively).
Figure 6B:
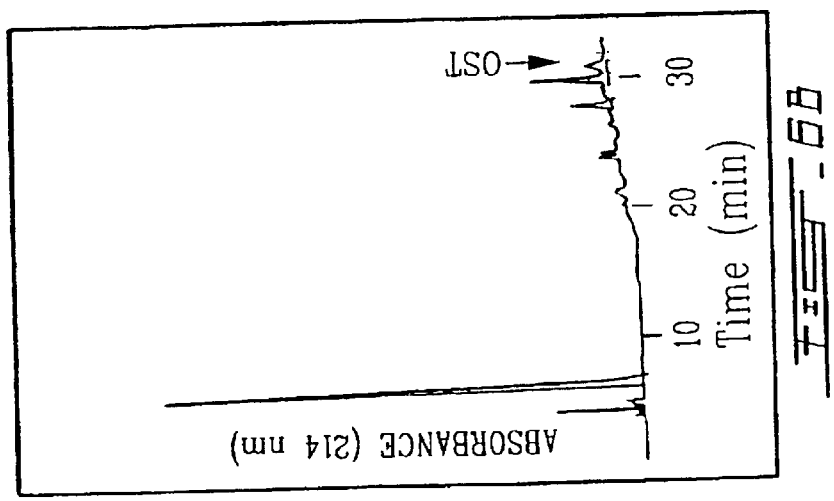
Figure 6A:
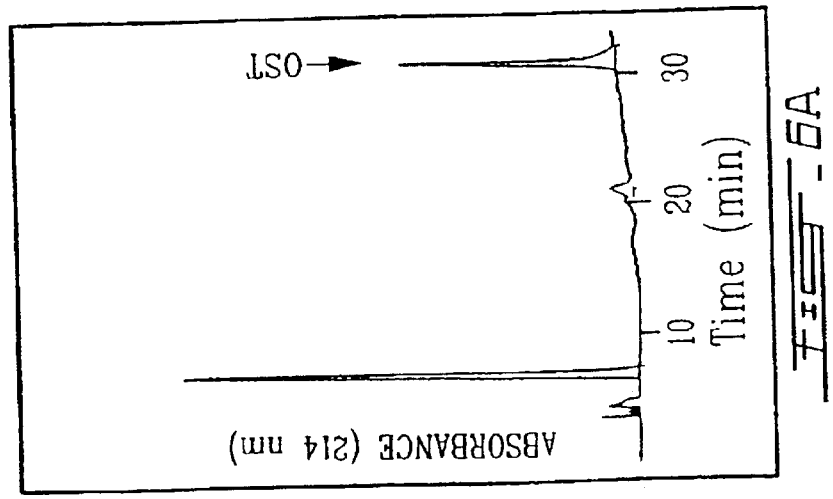
Figure 6F:
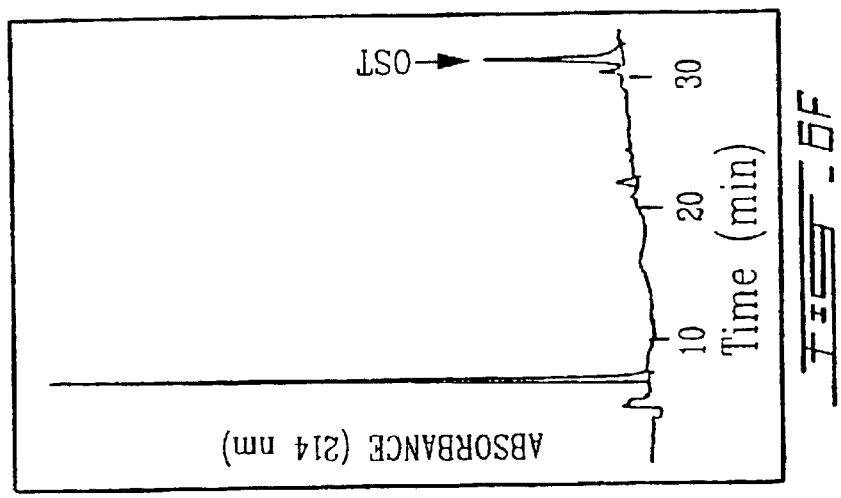
Figure 6E:
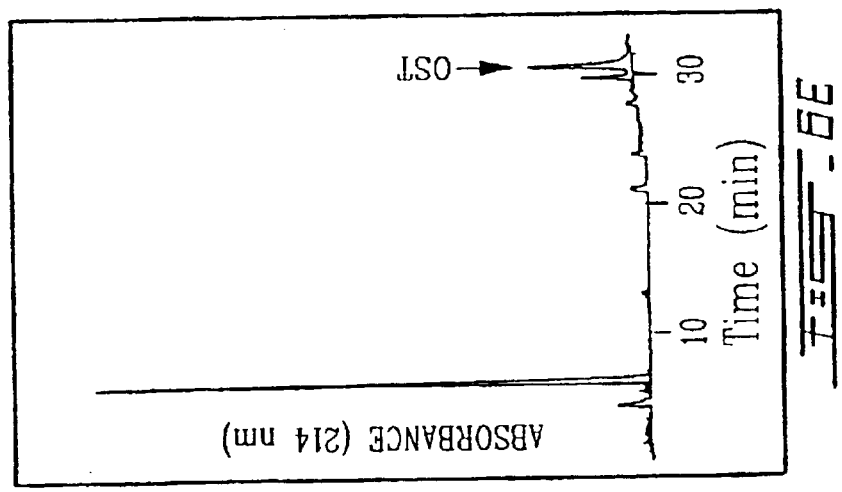
Figure 6D:
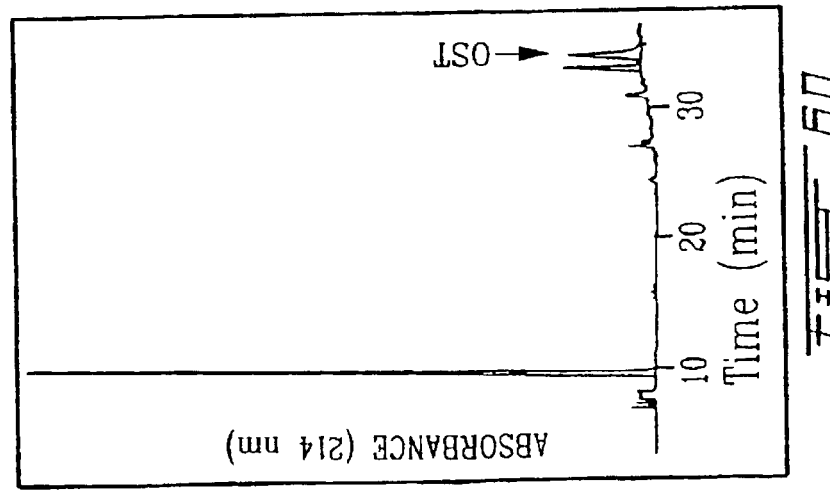
Figure 6G:
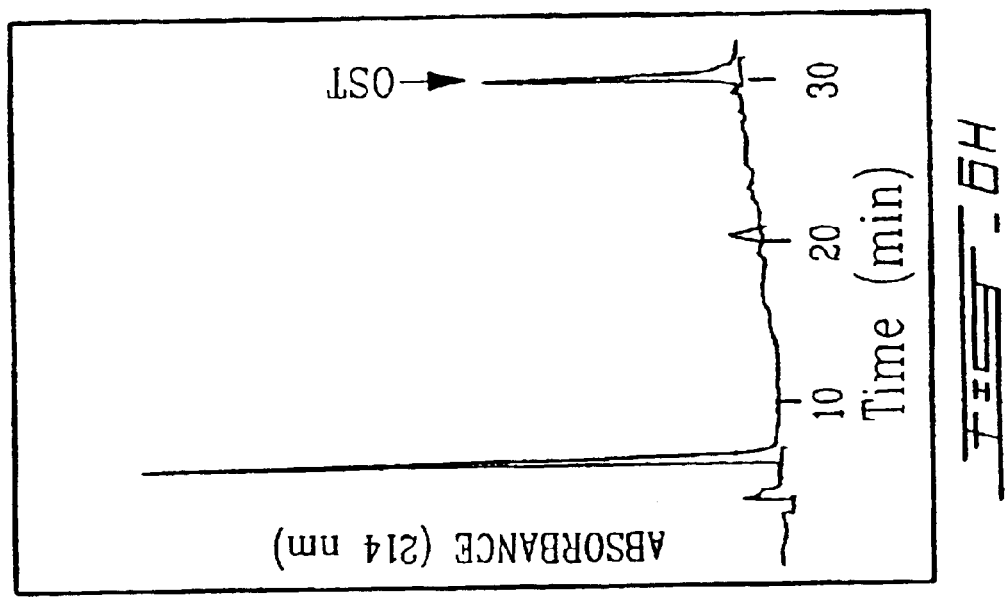
Figure 6H:
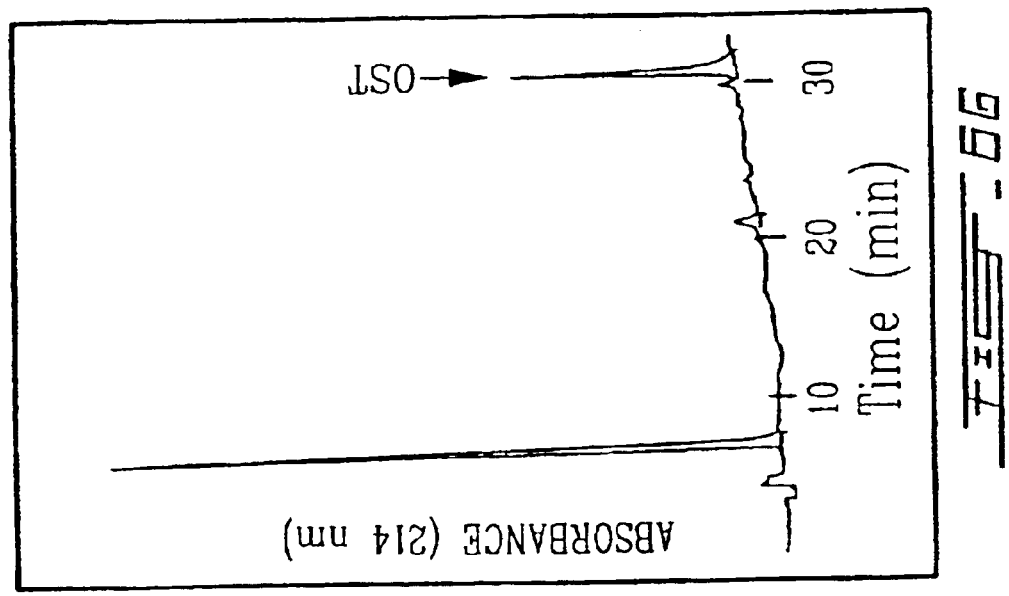

COS-1 cells were transfected with an expression vector containing the entire coding sequence of PHEX inserted downstream from the RSV promoter. This vector is called pCDNA3/RSV-PHEX-FLB (see Methods). The cells were kept in culture for 16 h after the transfection and a membrane fraction was prepared as explained in Methods. The expression of PHEX was monitored in Western blots with monoclonal antibody 15D7. As seen in FIG. 4 a band migrating with a mobility corresponding to an apparent Mr of 105,000 was observed in the membrane fraction of cells transfected with the pCDNA3/RSV-PHEX-FLB vector (lane 2). This band was absent from the extract of control cells (lane 1).

Production of a Soluble Form of Recombinant PHEX

We next wanted to determine whether it is possible to use genetic engineering techniques to promote the secretion of a soluble and active form of PHEX from transfected eukaryotic cells. Obviously, this kind of enzyme, which can easily be purified from the incubation medium of cultured cells without the use of detergent, would be very useful for further structural studies and inhibitor screening. It could also eventually be used as an injectable therapeutic agent or in topical applications to increase the rate of bone mineralization or bone healing.

PHEX is a class II integral membrane protein. Class II membrane proteins have, near their amino terminus, a unique hydrophobic peptide acting both as a signal peptide to direct the translocation of the protein through the membrane of the rough endoplasmic reticulum and as a transmembrane domain for anchoring the protein in the cell plasma membrane. Unlike class I membrane proteins which possess a cleavable signal peptide and are anchored in the membrane by an additional membrane-spanning hydrophobic sequence (also called Stop Transfer Sequence), class II membrane proteins cannot be easily transformed into soluble forms by deleting the hydrophobic transmembrane domain. In class II membrane proteins, deletion of the anchoring segment also removes the signal peptide, thereby preventing the translocation of the protein in the RER and its transport to the cell surface. Theoretically, there are two different approaches for transforming a membrane-bound class II protein into a soluble form: 1) the extracellular domain of the protein could be fused to a heterologous cleavable signal peptide; and 2) changes in the transmembrane domain could be introduced to transform the combined signal/anchor into a cleavable signal peptide. Both strategies were successfully used to produce a soluble from of NEP (Lemay et al., 1989; Lemire et al., 1997).

In this work, a PHEX secretion vector was first constructed by fusing inframe the sequence encoding the complete ectodomain of the human enzyme with the POMC signal peptide (FIG. 1A), these sequences being under the control of the RSV promoter. Despite the fact that PHEX immunoreactive material could be detected in the cell extract of transfected cells, expression levels were low and no enzyme could be found in the secretion medium (results not shown). When the cell-associated PHEX immunoreactive material was digested with endoglycosidases and analyzed by Western blot, it was found to be essentially endo H sensitive, indicating retention of the recombinant protein in the RER (results not shown).

Replacement of part of the transmembrane region (underlined sequence in in FIG. 1B: construct 1 (SEQ ID NO: 2)) by the underlined sequence shown on construct 2 (SEQ ID NO:3) resulted in the secretion of a soluble form of PHEX from transfected COS-1 cells (results not shown). The yield was further increased by deleting the sequence LFLV at the junction between the transmembrane and ectodomain (panel B: construct 3 SEQ ID NO: 4). FIG. 4 (lane 4) shows the amount of recombinant protein secreted in the incubation medium by transfected COS-1 cells. The same vector was also transfected in LLC-PK1 cells as described in Methods and stable transfectants were selected for their G-418 resistance. This pool of G-418 resistant cells was found to secrete substantial amounts of secPHEX (up to 600 µg/L) as seen by Western blotting (results not shown). SecPHEX was resistant to endo H, indicating that it had acquired terminal sugars, most probably during its transit through the Golgi apparatus (results not shown). The enzyme secreted by cultures of LLC-PK1 cells could then be purified either by immunoaffinity or by ion-exchange chromatography.

Preferred Purification of secPHEX by Ion-exchange Chromatography

Concentrated culture medium from secPHEX-transfected LLC-PK1 cells was loaded on SP-Sepharose column and proteins eluted as described in Methods. Monitoring of the eluate at 280 nm revealed one major protein peak (result not shown), which was shown by immunoblotting to contain secPHEX (FIG. 5). Analysis of the fractions containing secPHEX on 7.5% SDS-PAGE and detection of proteins in the gel by silver staining showed that secPHEX represented more than 90% of proteins present in the fractions. Typically, 1.25 mg of pure secPHEX are obtained from 600 ml of non-concentrated culture media.

Although secPHEX has been recovered from spent culture medium, it is feasible nowadays to have a host such as a ruminant, the organs of which are engineered to produce PHEX as a secretion product in milk, for example. A recombinant vector expressible in the tissue could comprise as an insert a construct similar to the one which led to the production of secPHEX in spent culture medium. Modifications to the construct are well known to the skilled artisan (promoter, signal peptide, etc). That recombinant vector is included in a composition and in a method for producing PHEX.

On the opposite, if PHEX needs to be silenced, anti-PHEX molecules are included in the compositions and methods of the present invention and their administration inhibits PHEX activity.

Purification of secPHEX by Immunoaffinity

Immunoblot analysis of the fractions obtained from the column showed that secPHEX was retained. However, Coomassie Blue staining showed that other proteins were also present in the fractions (results not shown). The amount of secPHEX obtained from 165 ml of non-concentrated LLC-PK1 culture medium was evaluated at 3 µg of protein.

Activity of secPHEX

HPLC analysis of PTHrP107-139 digested with secPHEX in conditions described in Methods revealed that secPHEX can degrade this peptide. PTHrP107-139 peak on the chromatogram was decreased to 15% of its original surface after only 15 min of incubation (FIG. 6). Peaks corresponding to metabolites appeared on the chromatogram. This enzymatic activity was fully inhibited by 0.001 M EDTA and 0.001 M O-phenantrolin, two general inhibitors of metallopeptidases. Activity was also observed in Acetate, HEPES and Tris buffers covering a pH range from 4.0 to 8.5. Phosphate buffer inhibited the activity of the enzyme (FIG. 6).

EXAMPLES

Example I

Use of Recombinant secPHEX to Identify its Natural Substrate in Bone

PHEX is expressed in osteoblasts, and its expression is temporally associated with the mineralization of the extracellular matrix in cultured osteoblasts (Beck et al., 1997a; Du et al., 1996a; Guo and Quarles, 1997a) and during development (Ruchon et al., 2000). These observations suggest that bone is a relevant site of PHEX expression and that a potential relationship exists between mutations of PHEX and aberrant osteoblast-mediated mineralization. Thus PHEX may function in osteoblasts to metabolize endogenous or exogenous factors that regulate the process of osteoblast-mediated mineralization. In support of this hypothesis, a recent report suggests that loss of PHEX function in cultured osteoblasts of Hyp mice is associated with the accumulation of a factor or factors that inhibit mineralization of extracellular matrix in vitro (Xiao et al., 1998). The availability of recombinant soluble PHEX greatly facilitates the identification of the physiological bone substrate(s) for PHEX in a series of experiments such as the one described hereunder.

Bones of Hyp mice are dissected, freed from connective tissue, and muscles frozen in liquid nitrogen and lyophilized. The bones are then crushed into a powder and extracted with a strongly acidic solution containing trifluoroacetic acid (TFA), formic acid and 1M NaCl. The composition of this solution is selected such as to inactivate all protease activities and avoid the solubilization of large molecular weight proteins. The acidic extract is then lyophilized and an aliquot containing approximately 100 µg of total peptide resuspended in a physiological buffer at pH around 7.0, is submitted to digestion with 1–10 µg of PHEX purified by ion-exchange or by immunoaffinity chromatography, as described above. A control experiment, where the enzyme preparation is inactivated by acidic or heat go treatment prior to the incubation, is conducted in parallel. The peptides contained in the samples are then separated by reversed-phase HPLC on a C 18µBondapak column using buffers containing 0.1% TFA and variable concentrations of acetonitrile (i.e. from 0 to around 80%). The chromatograms of the peptides digested with active or inactivated PHEX are compared. The mixture of bone peptides taken from Hyp mouse and incubated with the inactivated PHEX preparation should contain the PHEX substrate. Incubation of the same mixture with active PHEX however should allow the cleavage of the PHEX substrate into peptide metabolites. Comparison of the chromatograms should thus allow identifying peaks corresponding to PHEX substrate and its metabolites. These peaks are then collected and identified by mass spectrometry and/or automated Edman sequence degradation.

The identification of PHEX substrates may also be done using a similar strategy with conditioned medium taken from cultures of Hyp mouse osteoblasts.

Alternatively, an inactive soluble form of PHEX immobilized on a chromatographic support may be used as an affinity reagent for purifying PHEX substrates from crude extracts of tissues (such as bones) or serum. Cell surface metallopeptidases from the neprilysin family can be modified by the addition of a C-terminal extension without interfering with their enzymatic activity (Howell et al., 1995; Yang et al., 1995). A soluble form of PHEX, extended by an additional C-terminal peptide of approximately 20–25 amino acid residues (called here secPHEX-EC) is constructed by fusing in frame a synthetic oligonucleotide, as explained previously for NEP (Howell et al., 1995). The additional sequence is terminated by a cysteine residue such as to allow its efficient coupling to activated thiol-Sepharose 4B [agarose-(glutathione-2-pyridyl disulfide)] (Pharmacia, Fine Chemicals AB, Uppsala, Sweden). Sec-PHEX-EC is produced in high yields using, for example. the LLC-PK1 cell system used to produce secPHEX. The recombinant protein is purified by ion-exchange or immunoaffinity chromatography using conditions similar to the ones described for the purification of secPHEX. The fractions are analyzed by SDS-PAGE and the purity verified by staining with Coomassie blue.

For binding the purified recombinant protein to the solid phase, the Thiol-Sepharose resin is rehydrated to obtain approximately 1 ml of gel volume. The gel is equilibrated with a buffer A (0.1 M Bis-Tris, 0.5 M NaCl, pH 7.0) and incubated with approximately 3 mg of secPHEX-EC in buffer A (2–4 ml) overnight at 4° C. under constant agitation. The slurry is then washed, first with approximately 1 ml of buffer B (0.1 M Bis-Tris, 5 mM DTT, pH 7.0) and then extensively with buffer A. The quantity of proteins coupled to the support is determined by the Bradford assay (BioRad) on a small amount of gel.

The immobilized secPHEX-EC is used as a solid phase reagent for the screening of PHEX inhibitors. Enzymatically inactive variants of this material is also prepared by binding a form of secPHEX-EC carrying a mutation on the catalytic glutamic acid residue in position 581 to change it into a valine. A similar mutation in the coding sequence of NEP was previously shown to result in a catalytically inactive enzyme that nevertheless retained its full binding activity for inhibitors and substrates (Devault et al., 1988). Such an affinity reagent is used to bind and purify PHEX peptide substrates in crude tissue extracts. Receptors, if any, can be found using the same approach. Screening of inhibitor components can also be performed, although an active PHEX may be preferred. Tissue extracts prepared as described above are incubated under constant agitation in a buffer such as 0.1M Bis-Tris pH 7.5 with 1 ml of the affinity resin at 40° C. After washing in the same binding buffer, the bound peptides can be eluted from the gel by either raising or lowering the pH and/or by increasing the ionic strength of the buffer. Many other mutations may be envisaged, the purpose of which remains the replacement or elimination of the glutamic acid residue which is specific to the gluzincins. For example, valine has been tried with success as a substituting amino acid, but other amino acids such as hydrophobic, and preferably aliphatic, amino acids may be equivalent.

Example II

Enzymatic Assay

A peptide consisting of, for example, 10 amino acid residues spanning the cleavage site of PTHrP107-139 is synthesized by solid-phase peptide synthesis and used as a substrate for PHEX. The cleavage site is determined by assaying the enzymatic reaction products with a mass spectrometer equipped with a liquid sample inlet port, as found with LC-MS instruments, with the separation achieved in-line or off-line. This decapeptide (10 $\mu$g) is incubated in the presence of purified secPHEX (1–10 $\mu$g total protein). at 37° C. for 60 min in MES pH 6.5. The reaction is terminated by the addition of TFA to a final concentration of 0.1%. Metabolites are analyzed using a C-18$\mu$-Bondapack column (Waters). For example, metabolites may be resolved with a 45 min linear gradient of 0–40% acetonitrile in 0.1% trifluoroacetic acid at a rate of 1.0 ml/min. The eluted peptides are detected by monitoring their absorbance at 214 and 254 nm. The decapeptide should be cleaved into two shorter peptides that will be eluted at different retention times. The peak fractions corresponding to these two peptides are collected and their molecular mass is determined by mass spectrometry to identify the position of the cleavage site. Once validated as a substrate for PHEX, the synthetic peptide described here above may be modified such as to incorporate amino acid derivatives bearing either fluorescent groups, chromogenic groups or radioactive atoms. These peptides derivatives are then used to construct fast, sensitive and robust enzymatic assays for further quantifying and characterizing PHEX in tissue extracts, as described in Example III.

Example III

Screening for Quenched-fluorescent Substrate

The peptide identified in Example II is used to design and synthesize internally quenched fluorescent peptide substrates for PHEX. Small peptide libraries are prepared with a fluorophore at one extremity and a quencher group at the other (Meldal, 1998). The substrate can be identified using a strategy described in (Apletalina et al., 1998). For each hexapeptide library, the identity of one residue at one position remains constant while the rest is randomized (for a total of 6*20=120 individual libraries). Each library is comprised of 3.2 million different members and is identified both by the position of the constant residue along the hexapeptide, and its identity. A purified preparation of PHEX enzyme is added to each library and the fluorescence is recorded. The data is organized to identify the libraries producing the most fluorescence for each position along the hexapeptide. This arrangement suggests the identity of important residues at each position along the hexapeptide. Hexapeptides representing the best suggestions are prepared and tested in a similar fashion. From this set, the hexapeptide with the best fluorescence is selected. This assay can be useful for setting up a high throughput screening method for identifying inhibitors in combinatorial libraries of compounds.

Example IV

Uses of Recombinant PHEX Protein in Therapeutic Applications

The murine Hyp model reproduces the characteristics of human X-linked hypophosphatemia (XLH), an inherited disease causing renal loss of phosphate (Pi), severe rickets and osteomalacia. The presence of renal phosphate wasting due to a mutation in the PHEX gene suggests that this endopeptidase degrades a yet unidentified phosphaturic hormone, referred to as phosphatonin (Kumar, 1997). To test this hypothesis directly, primary mouse proximal tubule cell cultures (MPTC), expressing normal features of proximal tubule cells are prepared. The presence of 10% Hyp mouse serum in HAMF12/DMEM media (1 mM Pi) for the last 48 hours of culture of MPTC was previously found to reduce Pi uptake by 45.7 +/−3.9%, as compared with normal mouse serum, in a dose- and time-dependent manner (Lajeunesse et al., 1996). If defects in the PHEX gene in Hyp mouse osteoblasts are responsible for the release and/or the modification of a factor that can reach the circulation and inhibit renal phosphate re-absorption, it should be possible to abolish the effect of the Hyp mouse serum on Pi uptake by pretreating the serum with a purified preparation of PHEX. The effect of PHEX (1–10 $\mu$g of purified recombinant secPHEX) on Hyp mouse serum is then monitored by measuring phosphate uptake by MPTC cells. Control experiments include incubating the serum samples under similar conditions, but with heat or acid inactivated PHEX. If PHEX treatment is found to restore normal phosphate uptake, recombinant soluble PHEX might thus be used as a therapeutic agent for restoring normal phosphate levels, first in animal models (such as the Hyp mouse) and then in patients with pathological states characterized with X-linked hypophosphatemic rickets.

Patients suffering from oncogenic hypophosphatemic osteomalacia, a rare disorder, display abnormalities similar to those found with X-linked hypophosphatemic rickets patients. Therefore, normophosphatemia in these patients may be re-established with the administration of soluble PHEX enzyme.

Example V

Production and Use of PHEX Antibodies

As shown in the present work, knowledge of PHEX cDNA sequences can be used to raise specific antibodies. For example, regions of lesser homology. between the peptidases (amino acid residues 121 to 294) can be used to synthesize peptides whose sequences are deduced from the translation of the cDNAs. Alternatively, bacterially-expressed fragments of the cDNAs fused to GST, for example, may be purified and injected into rabbits or mice for polyclonal or monoclonal antibody production. These antibodies or derived "diagnostic reagents", which usually comprise labelled antibodies, can be used to:

Identify by immunohistochemistry the peptidergic pathways in which the peptidases are functioning;

Study the physiopathology of PHEX by immunoblotbng or immunohistochemistry on samples of biological fluids or biopsies;

Set up high through put screening assays to identify PHEX inhibitors.

This can be done, for example, by using the antibodies to attach the PHEX to a solid support;

Purify PHEX with said antibodies by immunoprecipitation or affinity chromatography by identifying antibodies capable of selectively binding to PHEX in one set of conditions and releasing it in another set of conditions, typically involving a large pH or salt concentration change without denaturing PHEX;

Identify antibodies that block PHEX activity and use them as therapeutic agents. Blocking antibodies can be identified by adding antisera or ascites fluid to an in vitro enzymatic assay as described in Example II and looking for inhibition of PHEX activity. Blocking antibodies may then be injected in normal and disease model animals to test for in vivo effects.

Example VI

Alternative Methods for Producing Recombinant Soluble PHEX Enzymes

As shown above, recombinant active PHEX enzymes can be obtained by expression of PHE)X cDNAs in mammalian cells. From past experience with another member of the family, neprilysin (Devault et al., 1988; Fossiez et al., 1992; Ellefsen, 1999), expression can also be performed in other expression systems after cloning of PHEX cDNA in appropriate expression vectors. These expression systems may include the baculovirus/insect cells or larvae system and the Pichia pastoris-based yeast system. Production of recombinant PHEX enzymes includes the production of naturally occurring membrane bound or soluble forms of the protein, or genetically-engineered soluble forms of the enzyme. The latter can be obtained by substituting the cytosolic and trans-membrane domain by a cleavable signal peptide, such as that of proopiomelanocortin, as done previously (Lemay et al., 1989a) or by transforming by genetic manipulations the non-cleavable signal peptide membrane anchor domain into a cleavable signal peptide, as done previously (Lemire et al., 1997a) or by fusion of the ectodomain of PHEX enzyme to the amino-terminal domain (from the initiator methionine to amino acid residue 300) of naturally occurring soluble NEP-like enzymes such as NL-1, as done in other work.

Example VII

Identification of Inhibitors

Inhibitors can be identified from synthetic libraries, biota extracts, the current literature and from rationally-designed inhibitors using X-ray crystallography and substituent activity relationships. Each molecule or extract fraction is tested for inhibitory activity using the enzymatic test described above. The molecule responsible for the largest inhibition is further tested to determine its pharmacological and toxicological properties following known procedures. In vitro inhibition of enzymatic PHEX degradation can be screened using any of several art-recognized in vitro models. In these models, a peptide ("substrate") is exposed to the PHEX enzyme. The substrate may either be a bone related peptide, a peptide known to be cleaved by any other family member or another peptidic substrate susceptible to degradation by the PHEX enzyme. Degradation of the peptide results in liberation of specific metabolites. The amount of metabolite liberated (or peptide maintained) can be monitored to determine the degree of degradation of the substrate by the enzyme. That is, PHEX enzyme inhibitors can be tested to determine their propensity to reduce the amount of metabolite liberated by degradation of a particular substrate by a particular enzyme.

These in vitro models generally consist of a test sample (containing a PHEX enzyme inhibitor and a peptidic substrate) and a control sample (containing the substrate with no PHEX inhibitor). Each sample is exposed to a particular inhibitor, and the samples are then compared to determine whether significantly more metabolite (or less substrate) is present in the control sample than in the test sample. If there is significantly more metabolite (or less substrate) in the control sample than the test sample, the test compound is an inhibitor of the enzyme(s) present. One such method is described above.

There is an extensive literature available on Zn metallopeptidases (Roques 1982a, Roques 1982b, Ondetti 1984, Roques 1985, Roques 1986, Chipkin 1986, Thorsett 1987, Rich 1990, Vallee 1990) as potent inhibitors of Neprilysin (NEP). Among the many known functional groups able to coordinate the $Zn^{++}$ cation, the thiol, carboxyl, hydroxamyl and phosphoryl groups have all been used with success in the development of ACE and NEP inhibitors. All such molecules that display inhibitory activity of the PHEX enzyme (PHEX inhibitors) are encompassed by the present invention.

As indicated above, PHEX is a member of a family of enzymes that share similar properties, such as their sensitivity to the same inhibitor and their ability to process the same substrates. Numerous PHEX enzyme inhibitors and methods for their preparation are described in the literature and are useful in the methods of the present invention. Such inhibitors are described in the following references, all of which are incorporated herein by reference: U.S. Pat. No. 4,380,535, to Sarantakis, issued Apr. 19, 1983; U.S. Pat. No.

4,423,242. to Wilkinson et al., issued Dec. 27, 1983; U.S. Pat. No. 4,474,795, to Greenberg et al., issued Oct. 2, 1984; U.S. Pat. No. 4,504,492. to Wilkinson et al., issued Mar. 12, 1985; U.S. Pat. No. 4,513,009, to Roques et al., issued Apr. 23, 1985; U.S. Pat. No. 4,514,391, to Gordon et al., issued Apr. 30, 1985; U.S. Pat. No. 4,528,296, to Vecchietti et al., issued Jul. 9, 1985; U.S. Pat. No. 4,552,866, to Delaney et al., issued Nov. 12, 1985; U.S. Pat. No. 4,567,198, to Delevallee et al., issued Jan. 28, 1986; U.S. Pat. No. 4,610,816, to Berger, issued Sep. 9, 1986; U.S. Pat. No. 4,611,002, to Ondetti, issued Sep. 9, 1986; U.S. Pat. No. 4,618,708, to Roques et al., issued Oct. 21, 1986; U.S. Pat. No. 4,636,522, to Gordon, issued Jan. 13, 1987; U.S. Pat. No. 4,670,541, to Delaney et al., issued Jun. 2, 1987; U.S. Pat. No. 4,681,960, to Kakimoto et al., issued Jul. 21, 1987; U.S. Pat. No. 4,721,726, to Berger, issued Jan. 26, 1988; U.S. Pat. No. 4,722,810, to Delaney et al., issued Feb. 2, 1988; U.S. Pat. No. 4,939,261, to Ksander, issued Jul. 3, 1990; U.S. Pat. No. 5,096,925, to Ksander, issued Mar. 17, 1992; U.S. Pat. No. 5,098,934, to Vevert et al., issued Mar. 24, 1992; U.S. Statutory Invention Registration No. 11642, Floyd et al., published Jun. 6, 1989; United Kingdom Patent Publication 8111322, Wilkinson, published Nov. 4, 1981; United Kingdom Patent Publication, Wilkinson et al., published Apr. 7, 1983; European Patent Publication 161,769, Delaney et al., published Nov. 21, 1985; European Patent Publication 341,081, Kawamura et al., published Nov. 8, 1989; European Patent Publication 474,553, Shibahara et al., published Mar. 11, 1992; PCT Patent Publication 92/03410, Neustadt et al., published Mar. 5, 1992; Foumie-Zaluski et al., 'Differential Recognition of 'Enkephalinase' and Angiotensin-Converting Enzyme by New Carboxylalkyl Inhibitors", 31 Life &L 2947–2954 (1982); Mimura et al., "A Novel Class of Enkephalinase Inhibitors Containing a C-Terminal Sulfo Group", 35.!. Med. Chem. 602–608 (1992).

Preferred PHEX enzyme inhibitors useful in the methods of the present invention have the general structure of formula (I):

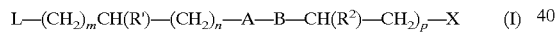

L—$(CH_2)_m$CH(R')—$(CH_2)_n$—A—B—CH($R^2$)—$(CH_2)_p$—X    (I)

wherein
(1) L is —S—$R^3$ or —C(=O)—$R^4$ where $R^3$ is hydrogen or —C(=O)—$R^5$, where $R^5$ is lower alkyl; and where $R^4$ is hydroxy or —NHOH;
(2) $R^1$ is hydrogen, lower alkyl, aryl, arylalkyl;
(3) A is —C(=O)—, —NH—C(=O)—, or —N($R^6$), where $R^6$ is hydrogen or lower alkyl;
(4) B is —NH—, —O—, —S—, or —C(=O)—
(5) $R^2$ is hydrogen, lower alkyl, aryl, arylalkyl (preferably phenylmethyl);
(6) X is —C(=O)—NH—$R^7$ or —C(=O)—O—$R^7$ where $R^7$ is hydrogen, lower alkyl, phenyl, or arylalkyl;
(7) m is from 0 to about 2;
(8) n is 0 or I (preferably 0); and
(9) p is from 0 to about 4 (preferably 0 or 1);
and pharmaceutically-acceptable salts thereof.

Other preferred PHEX inhibitors have the general structure (II):

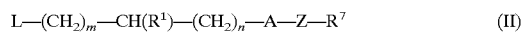

L—$(CH_2)_m$—CH($R^1$)—$(CH_2)_n$—A—Z—$R^7$    (II)

wherein:
(1) L, $R^1$, A, m, and n are as described in formula (I);
(2) Z is —NH—, —O—, —S—, —C(=O)—, or nil; and (3) $R^7$ is a carbocyclic ring or a heterocyclic ring; preferably benzenesulfonic acid, pyridyl, or morpholinyl;
and pharmaceutically-acceptable salts thereof.

Other preferred PHEX inhibitors, as described in U.S. Pat. No. 4,721,726, to Berger, issued Jan. 26, 1988, have the general structural formula (III):

$R_1$CH(CO$R_2$)—NH—CH$R_3$—CONH(CH$_2$)C$R_4R_5$—CO$R_6$    (III)

and the racemates, enantiomers and diastereoisomers thereof, as well as the pharmaceutically acceptable salts thereof wherein:

$R_1$ is alkyl having from 1 to 6 carbon atoms, adamantylmethyl, cycloakylmethyl having from 4 to 8 carbon atoms or A—$X_m$—$C_nH_{2n}$— wherein X is oxygen or sulfur, A is phenyl which may be substituted with the group, Y, where Y is halogen, hydroxy, trifluoromethyl, alkoxy having from I to 6 carbon atoms, alkyl having from I to 6 carbon atoms, 2- and 3-furanyl, 2- and 3thienyl, or phenyl (which may be substituted with halogen, hydroxy, trifluoromethyl, alkoxy having from I to 6 carbon atoms or alkyl having from 1 to 6 carbon atoms) benzyl (the phenyl ring of which may be substituted with the group, Y, as defined herein), 1- and 2-naphthyl, 2- and 3-furanyl or 2- and 3-thienyl; m is 0 or 1 and n is 0, 1, 2, 3, or 4;

$R_2$ and $R_6$ may be the same or different and are hydroxy, alkoxy having from 1 to 8 carbon atoms, B—$X_m$—$C_nH_{2n}$—O— wherein B is phenyl (which may be substituted with the group, Y, as defined herein) or 1- and 2-naphthyl, X, m, and n are as defined herein provided that when n=0, m=0, —OCH$_2$OCO-alkyl having from 3 to 8 carbon atoms, —OCH$_2$CO-Phenyl (the phenyl ring of which may be substituted with the group, Y, as defined herein), 1-glyceryl,

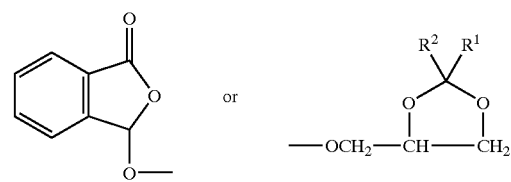

or    —OCH$_2$—CH—CH$_2$ wherein $R_7$ is hydrogen, alkyl having from 1 to 6 carbon atoms, or phenyl which may be substituted with the group, Y, as defined herein, and $R_8$ hydrogen or alkyl having from 1 to 6 carbon atoms;

$R_2$ may also be —N$R_7R_8$ wherein $R_7$ and $R_8$ are as defined herein;

$R_3$ is alkyl having from I to 6 carbon atoms, cycloakylmethyl having from 4 to 8 carbon atoms, 2- and 3-thienylmethyl, 2- and 3-furanylmethyl, 1- and 2-naphthylmethyl, or benzyl the phenyl ring of which may be substituted with the group, Y, as defined herein;

$R_4$ is D—$C_nH_{2n}O_m$— wherein D is hydrogen, alkyl having from I to 4 carbon atoms or phenyl which may be substituted with the group, Z, wherein Z is halogen, hydroxy, trifluoromethyl, alkoxy having from I to 6 carbon atoms, or alkyl having from 1 to 6 carbon atoms; m and n are as defined herein;

$R_4$ may also be —N$R_5$CO$R_7$ (wherein $R_5$ and $R_7$ are defined herein), and —N$R_5$CO$_2R_9$ (wherein $R_5$ is defined herein and $R_9$ is alkyl having from 1 to 6 carbon atoms or phenyl which may be substituted with the group Y, as defined herein) provided that p is 1 or 2;

R$_5$ is hydrogen or alkyl having from 1 to 6 carbon atoms; and p is 0, 1 or 2.

Other preferred PHEX enzyme inhibitors, as described by Mimura et al., "A Novel Class of Enkephalinase Inhibitors Containing a C-Terminal Sulfo Group", 351. *Med. Chem.* 602–608, have the general structure (IV):

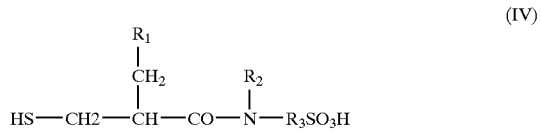

(IV)

wherein:

R$_1$ is selected from phenyl, p-methylphenyl, pmethoxyphenyl, p-fluorophenyl, p-trifluoromethylphenyl, p-nitrophenyl, p-dimethylaminophenyl, p-phenylphenyl, phenylethyl, 1-naphthtyl, 3-pyridyl, I,2-benzisoxazol-3-yl, or 1methylethyl;

R$_2$ is selected from hydrogen or cyclopropyl; and

R$_3$ is selected from CR$_2$, CH$_2$—CH$_2$, CH$_2$—CH$_2$—CH$_2$, CH(CH$_3$), CH(CH$_2$CH(CH$_3$)$_2$), o-phenyl, m-phenyl, p-phenyl, p-phenylmethyl, and 1,4-naphthylene. Particularly preferred PHEX enzyme inhibitors useful in the methods of the present invention include (DL-3-mercapto-2-benzylpropanoyl)-glycine; 1-(DL-3-mercapto-2-methylpropanoyl)-L-proline; 2-benzyl-3-(N-hydroxycarboxamido)-propanoyl-L-alanine; 2-benzyl-3-(N-hydroxycarboxamido)-propanoyl-L-phenylalanine; (±)-N-(2-acetylthio)methyl-1-oxo-3-phenylpropyl glycine benzyl ester; N-morpholinyl-2-phenylmethyl-3-mercaptopropanamide; alpha-(mercap-tomethyl)-N-(4-pyridyl) benzenepropanamide; N-[2-benzyl-3-(N-hydroxy-carboxamido)propanoyl]-3-amino-4-phenylbutyric acid; N-[(R,S)-2-benzyl-3-[(S)(2-amino-4-methylthio)butyldithio]-1-oxopropyl]-L-Phe-benzyl ester; N-(2-benzyl-3-mercaptopropanoyl)metanilic acid; and N-[(R,S)-2carboxy-3-phenyl-propanoyl]-L-Leu.

The inhibitor with the best distribution, pharmacological action combined with low toxicity will be selected for drug manufacturing. Pharmaceutically acceptable formulation of the inhibitor or its acceptable salt will be prepared by mixing with known excipients to produce tablets, capsules or injectable solutions. Between 1 and 500 mg of the drug is administered to the patients.

Example VIII

Therapeutic Uses

The present invention also provides methods of treatment for hyperphosphatemia, including its most frequent manifestations, secondary hyperparathyroidism and renal osteodystrophy. The method comprises the administration of a PHEX inhibitor that induces a reduction in circulating phosphate, thus reducing, or preferably preventing, hyperphosphatemia and the appearance of its most frequent consequences.

As indicated above, PHEX is member of a family of metalloproteases that shares similar properties including, as indicated above, their sensitivity to the same inhibitor and their capability of processing the same substrates. Numerous NEP-like enzyme inhibitors, and methods for their preparation, are described in the literature and are useful in the methods of the present invention.

The PHEX inhibitors that show inhibitory activity are administered to rats weighing about 250 g at a dose of 1 mg/kg. The control group consists of another group of rats where the same vehicle is administered without the PHEX inhibitor. Serum and urine are obtained from the test animals using standard methods. Phosphate concentration in serum and in urine is then measured by standard methods. PHEX inhibitors capable of inducing a change in phosphate concentration are said to be hypophosphatemic. Such compounds are the preferred "hypophosphatemic PHEX inhibitors" for the purpose of treating hyperphosphatemic patients.

The "least effective dose" is the minimum dose that is required to induce a significant reduction in serum phosphate or PTH concentration. Preferably, the therapy will be initiated with such a dose. The treatment preferably involves the administration of a "hypophosphatemic PHEX inhibitor" for a period of time sufficient to achieve a reduction in phosphate or PTH blood concentration or both (here and after the blood parameters). Preferably, the net reduction is about 25% of the difference between the patient value and that of the normal population or, more preferably, at least about 50% of the difference between the patient's value and that of the normal population. The specific period of time sufficient to achieve this reduction in the subject blood parameters may depend on a variety of factors. Such factors include, for example, the specific hypophosphatemic inhibitor employed, the amount administered, the age and gender of the subject, the specific disorder to be treated, concomitant therapies employed (if any), the general physical health of the subject (including the presence of other disorders), the severity of the disease in the individual, and the nutritional habits of the individual.

According to the methods of this invention, "administering" refers to any method which, in sound medical practice, delivers the hypophosphatemic inhibitor used in this invention to the subject to be treated in such a manner so as to be effective in achieving a reduction in the blood parameters. The hypophosphatemic PHEX enzyme inhibitor may be administered by any of a variety of known methods of administration, e.g., orally, dermatomucosally (for example, dermally, sublingually, intranasally, and rectally), parenterally (for example, by subcutaneous injection, intramuscular injection, intra-articular injection, intravenous injection), and by inhalation. Thus, specific modes of administration include, for example, oral, transdermal, mucosal, sublingual, intramuscular, intravenous, intraperitoneal, subcutaneous administration, and topical application. A preferred mode, for delivering the hypophosphatemic PHEX enzyme inhibitors is orally, for as long and as frequently as medically required. The period and frequency is adjusted after regular measurement of serum phosphate, PTH and vitamin D metabolites.

Thus, a preferred method of this invention comprises the steps of performing a diagnostic on a human subject for the detection of hyperphosphatemia, including its most frequent manifestations, secondary hyperparathyroidism and renal osteodystrophy and, upon obtaining a positive result from said diagnostic, administering the hypophosphatemic PHEX enzyme inhibitor according to the methods of this invention. Suitable diagnostics for the detection of hyperphosphatemia, including its most frequent manifestations, secondary hyperparathyroidism and renal osteodystrophy, are well known in the art. Such methods include the measurement of the blood, serum, plasma or urinary phosphate or the measurement of the blood, serum or plasma PTH.

Example IX

Dosage Forms

The hypophosphatemic PHEX enzyme inhibitors described herein may be administered in any of a variety of pharmaceutically acceptable compositions. Such compositions may comprise an active and a pharmaceutically acceptable carrier. Accordingly, for example, compositions for administering the hypophosphatemic PHEX enzyme inhibitor comprise:

(a) From about 1.0 mg to about 1000.0 mg of a hypophosphatemic PHEX enzyme inhibitor; and (b) A pharmaceutically acceptable carrier.

Pharmaceutically-acceptable carriers include solid or liquid filler diluents or encapsulating substances, and mixtures thereof, that are suitable for administration to a human or lower animal. The term "compatible", as used herein, means that the components of the pharmaceutical composition are capable of being co-mingled with the hypophosphatemic PHEX enzyme inhibitor, and with each other, in a manner such that there is no interaction, which would substantially reduce the pharmaceutical efficacy of the pharmaceutical composition under ordinary use situations. Pharmaceutically acceptable carriers must, of course, be of sufficiently high purity and sufficiently low toxicity to render them suitable for administration to the humans or lower animals being treated.

Some examples of the substances which can serve as pharmaceutical carriers are: sugars, such as lactose, glucose and sucrose; starches, such as corn starch and potato starch; cellulose and its derivatives, such-as sodium carboxymethylcellulose, ethylcellulose, cellulose acetate; powdered tragacanth; malt; gelatin; talc; stearic acid; magnesium stearate; vegetable oils, such as peanut oil, cottonseed oil, sesame oil, olive oil, corn oil and oil of theobroma; polyols such as propylene glycol, glycerin, sorbitol, mannitol, and polyethylene glycol; agar; alginic acid; pyrogen-free water; isotonic saline; phosphate buffer solutions; wetting agents and lubricants such as sodium lauryl sulfate; coloring agents; flavoring agents; and preservatives. Other compatible pharmaceutical additives and hypophosphatemic PHEX enzyme inhibitor may be included in the pharmaceutically acceptable carrier for use in the compositions of the present invention.

The choice of a pharmaceutically-acceptable carrier to be used in conjunction with the active substance is determined by the way the active substance is to be administered. If the active is to be injected, the preferred pharmaceutical carrier is sterile water, physiological saline, or mixtures thereof. The pH of such parenteral composition is preferably adjusted to about 7.4. Suitable pharmaceutically acceptable carriers for topical application include those known in the art for use in creams, gels, tapes, patches, and similar topical delivery means.

The pharmaceutically-acceptable carrier employed in conjunction with the hypophosphatemic PHEX enzyme inhibitor is used at a concentration sufficient to provide a practical size to dosage relationship. The pharmaceutically-acceptable carriers, in total, may comprise from about 0.1% to about 99.9% by weight of the pharmaceutical compositions of the present invention, preferably from about 5% to about 80%, and most preferably from about 10% to about 50%.

As indicated, the preferred method of administering hypophosphatemic PHEX enzyme inhibitor is dependent upon the class of active being administered. For the hypophosphatemic PHEX inhibitors, the preferred method of administration is orally, in a unit-dosage form (i.e., a dosage form containing an amount of active suitable for administration in one single dose, according to sound medical practice).

Preferred unit dosage forms include tablets, capsules, suspensions, and solutions, comprising a safe and effective amount of active. Pharmaceutically-acceptable carriers suitable for the preparation of unit dosage forms for oral administration are well known in the art. Their selection will depend on secondary considerations like taste, cost, shelf stability, which are not critical for the purposes of the present invention, and can be made without difficulty by a person skilled in the art. Preferably, oral unit dosage forms of the hypophosphatemic PHEX enzyme inhibitor comprise from about 1.0 mg to about 1000 mg of the inhibitor.

The present invention is intended to further encompass the following: (1) diagnostic kits for detecting the presence or amount of PHEX in a sample; (2) a method for detecting the presence or amount of PHEX-in a sample; (3) devices for purifying PHEX or mutants thereof; (4) devices for screening PHEX ligands; and (5) a method for obtaining a PHEX ligand. More particularly, the diagnostic kits comprise antibodies and/or a soluble PHEX enzyme. Antibodies againts PHEX may be used in devices for purifying PHEX, and PHEX or mutants thereof may be used in devices for screening PHEX ligands. Though not described herein, the more general aspects concerning the operability of the diagnostic kits and devices included in the present invention are known in the art and readily available.

The method for detecting the presence or amount of PHEX comprises the following steps:

contacting a sample containing PHEX with an antibody in conditions such that immune complexes can form; and detecting the immune complexes as an indication of the presence or amount of PHEX in the sample.

The method for obtaining a PHEX ligand comprises the following steps: contacting a sample containing one or more molecules with a PHEX mutant enzyme in conditions such that binding of the molecules with PHEX can occur;

detecting the binding of the molecules with PHEX as an indication of the presence of a PHEX ligand in the sample; and selecting the PHEX ligand.

Although not described in detail, the particulars relating to experimental conditions for carrying out the methods described above are within the purview of those skilled in the art and readily appreciable by them.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

REFERENCE LIST

Almaden Y, Canalejo A, Hernandez A, Ballesteros E, Garcia-Navarro S, Torres A and Rodriguez M (1996) Direct effect of phosphorus on PTH secretion from the whole rat parathyroid glands in vitro. J Bone Miner Res Jul 11:7 970–6

Apletalina, E., Appel, J., Lamango, N. S., Houghten, R. A., and Lindberg, I. (1998). Identification of inhibitors of prohormone convertases 1 and 2 using a peptide combinatorial library. J.Biol.Chem. 273, 26589–26595.

Beck, L., Soumounou, Y., Martel, J., Krishnamurthy, G., Gauthier, C., Goodyer, C. G., and Tenenhouse, H. S. (1997). Pex/PEX tissue distribution and evidence for a deletion in the 3' region of the Pex gene in X-linked hypophosphatemic mice. J.Clin.Invest. 99, 1200–1209.

Blais, A., Bissonnette, P., and Berteloot, A. (1987). Common characteristics for Na+dependent sugar transport in Caco-2 cells and human fetal colon. J.Membr.Biol. 99, 113–125.

Borle AB and Clark I (1981) Effects of phosphate-induced hyperparathyroidism and parathyroidectomy on rat kidney calcium in vivo. Am J Physiol August 241:2 E136–41

Chipkin, R. E.: Inhibitors of enkephalinase: the next generation of analgesics. Drugs Future 11: 593–606, 1986.

Crine, P., Dion, N., and Boileau, G. (1997). Endopeptidase-24.11. In Cell-Surface Peptidases in Health and Disease. A. J. Kenny and C. M. Boustead, eds. (Oxford: BIOS Scientific Publishers), pp. 79–98.

Demeter J G, De Jong S A, Oslapas R, Ernst K, Hessel P, Jarosz H, Smith M, Nayyar R, Lawrence A M and Paloyan E (1991) High phosphate diet-induced primary hyperparathyroidism:an animal model. Surgery December 110:6 1053–60.

Devault, A., Lazure, C., Nault, C., Le Moual, H., Seidah, N. G., Chrétien, M., Kahn, P., Powell, J., Mallet, J., Beaumont, A., Roques, B. P., Crine, P., and Boileau, G. (1987). Amino acid sequence of rabbit kidney neutral endopeptidase 24.11 (enkephalinase) deduced from a complementary DNA. EMBO J. 6, 1317–1322.

Devault, A., Nault, C., Zollinger, M., Fournié-Zaluski, M.-C., Roques, B. P., Crine, P., and Boileau, G. (1988). Expression of neutral endopeptidase (enkephalinase) in heterologous COS-I cells. Characterization of the recombinant enzyme and evidence for a glutamic acid residue at the active site. J.Biol.Chem. 263, 4033–4040.

Du, L., Desbarats, M., Viel, J., Glorieux, F. H., Cawthorn, C., and Ecarot, B. (1996). cDNA cloning of the murine Pex gene implicated in X-linked hypophosphatemia and evidence for expression in bone. Genomics 36, 22–28.

Ecarot, B., Glorieux, F. H., Desbarats, M., Travers, R., and Labelle, L. (1992). Effect of dietary phosphate deprivation and supplemetation of recipient mice on bone formation by transplanted cells from normal and X-linked hypophosphatemic mice. J.Bone Miner.Res. 7, 523–530.

Ellefsen (1999). Immobilization d'une forme chimérique soluble de l'endopeptidase neutre—24.11 sur un support chromatogaphique et mise au point d'un test de liaison. Mémoire de maitrise Université de Montréal.

Fossiez, F., Lemay, G., Labonté, N., Parmentier-Lesage, F., Boileau, G., and Crine, P. (1992). Secretion of a functional soluble form of neutral endopeptidase-24.11 from a baculovirus-infected insect cell line. Biochem.J. 284, 53–59.

Francis, F., Hennig, S., Korn, B., Reinhardt, R., De Jong, P., Poustka, A., Lehrach, H., Rowe, P. S. N., Goulding, J. N., Summerfield, T., Mountford, R., Read, A. P., Popowska, E., Pronicka, E., Davies, K. E., O'Riordan, J. L. H., Econs, M. J, Nesbitt, T., Drezner, M. K., Oudet, C., Pannetier, S., Hanauer, A., Strom, T. M., and Meindl, A (1995). A gene (PEX) with homologies to endopeptidases is mutated in patients with X-linked hypophosphatemic rickets. Nature Genet. 11, 130–136.

Grieff, M., Mumm, S., Waeltz, P., Mazzarella, R., Whyte, M. P., Thakker, R. V., and Schlessinger, D. (1997). Expression and cloning of the human X-linkod hypophosphatemia gene cDNA. Biochemical & Biophysical Research Communications 231, 635–639.

Guo, R. and Quarles, L. D. (1997). Cloning and sequencing of human PEX from a bone cDNA library: Evidence for its developmental stage-specific regulation in osteoblasts. J.Bone Miner.Res. 12, 1009–1017.

Howell, S., Lanctôt, C., Cailler, F., and Crine, P. (1995). Addition of a glycosylphosphatidylinositol anchor to a soluble form of neutral endopeptidase reestablishes its apical targeting in LLC-PKI cells. The Biochemical Society Meeting 657, 41–41.(Abstract)

Kates D M, Sherrard D J and Andress D L (1997) Am J Kidney Dis Dec 30:6 809–13

Korth, P., Egidy, G., Parnot, C., LeMoullec, J. M., Corvol, P., and Pinet, F. (1997). Construction, expression and characterization of a soluble form of human endothelin-converting-enzyme-1. FEBS Lett. 417, 365–370.

Kumar, R. (1997). Phosphatonin-a new phosphaturetic hormone? (lessons from tumourinduced osteomalacia and X-linked hypophosphataemia) [editorial]. Nephrol.Dial.Transplant. 12, 11–13.

Lajeunesse, D., Meyer, R. A. J., and Hamel, L. (1996). Direct demonstration of a humorally-mediated inhibition of renal phosphate transport in the Hyp mouse. Kidney Int. 50, 1531–1538.

Lemay, G., Waksman, G., Roques, B. P., Crine, P., and Boileau, G. (1989). Fusion of a cleavable signal peptide to the ectodomain of neutral endopeptidase (EC 3.4.24.11) results in the secretion of an active enzyme in COS-1 cells. J.Biol.Chem. 264, 15620–15623.

Lemire, I., Lazure, C., Crine, P., and Boileau, G. (1997). Secretion of a type II integral membrane protein induced by mutation of the transmembrane segment. Biochem.J. 322, 335–342.

Lipman, M. L., Panda, D., Bennett, H. P., Henderson, J. E., Shane, E., Shen, Y. N., Goltzman, D., and Karaplis, A. C. (1998). Cloning of human PEX cDNA. Expression, subcellular localization, and endopeptidase activity. J.Biol.Chem. 273, 13729–13737.

Meldal, M. (1998). Intramolecular fluorescence-quenched substrate libraries. Methods Mol.Biol. 87:65–74, 65–74.

Nelson, A. E., Mason, R. S., and Robinson, B. G. (1997). The PEX gene: not a simple answer for X-linked hypophosphataemic rickets and oncogenic osteomalacia. Mol. Cell.Endocrinol. 132, 1–5.

Meyer, R A Jr, Gray R W and Meyer M H. 1980. Abnormal vitamin D metabolism in the X-linked hypophosphatemic mouse. Endocrinology, 107:1577–1581.

Ondetti, M. A., and Cushman, D. W.: Angiotensin-converting enzyme inhibitors: biochemical properties and biological action. Crit. Rev. Biochem. 16: 381–411, 1984.

Rasmussen, H. and Tenenhouse, H. S. (1995). Mendelian hypophosphatemias. In The metabolic and Molecular Basis of Inherited disease. C. L. Scriver, A. L. Beaudet, W. S. Sly, and D. Valle, eds. (New York: McGraw Hill), pp. 3717–3745.

Rich, D. H.: Peptidase inhibitors. In comprehensive Medicinal Chemistry. The Rational Design, Mechanistic Study and Therapeutic Application of Chemical Compounds, ed. by P. G. Sammes and J. B. Taylor, Vol.2, p.391, Pergamon Press, New York, 1990.

Rifas, L., Dawson, L. L., Halstead, L. R., Roberts, M., and Avioli, L. V. (1994). Phosphate transport in osteoblasts from normal and X-linked hypophosphatemic mice. Calcif.Tissue Int. 54, 505–510.

Roques, B. P., Fournié-Zaluski, M. C., Florentin, D., Waksman, G., Sassi, A., Chaillet, P., Collado, H., and Constantin, J.: New enkephalinase inhibitors as probes to differentiate "enkephalinase" and angiotensin-converting-enzyme active sites. Life Sci. 31: 1749–1752, 1982a.

Roques, B. P., Fournié-Zaluski, M. C., Gacel, G., Lucas-Soroca, E., David, M., Schwartz, J. C., Malfroy, B., Llorens, C., Swerts, J. P., Lecomte, J. M., Meunier, J. C., Moisand, C., Morgat, J. L., and Maigret, B.: Sypthése et études physicochimiques et biologiques de ligands spécifiques des récepteurs enkephalinergiques mu et delta et d'inhibiteurs du systéme de dégradation des enképhalines endogénes. Acta Chim. Ther. 9: 211–240, 1982b.

Roques, B. P., and Fournié-Zaluski, M. C.: A new way to antinociceptive compounds through rational design of enkephalin degrading enzymes inhibitors. In Proceedings of the International Symposium on Medicinal Chemistry ed. by R. Dalhbom and J. L. G. Nilsson, pp. 134–146, Swedish Pharmaceutical Press, Stockholm, Sweden, 1985.

Roques, B. P., and Fournié-Zaluski, M. C.: Enkephalin degrading enzyme inhibitors: a physiological way to new analgesics and psychoactive agents. Natl. Inst. Drug Abuse Res. Monogr. Ser. 70: 128–154, 1986.

Ruchon, A. F., Marcinkiewicz, M., Siegfried, G., Tenenhouse, H. S., DesGroseillers, L., Crine, P., and Boileau, G. (1998). Pex mRNA is localized in developing mouse osteoblasts and odontoblasts. J.Histochem.Cytochem. 46, 459–468.

Strom, T. M., Francis, F., Lorenz, B., Boddrich, A., Econs, M. J., Lehrach, H., and Meitinger, T. (1997). Pex gene deletions in Gy and Hyp mice provide mouse models for X-linked hypophosphatemia. Hum.Mol.Genet. 6, 165–171.

Tenenhouse H S, Yip A and Jones G., 1988, Increased renal catabolism of 1,25-dihydroxyvitamin D3 in murine X-linked hypophosphatemic rickets. J. Clin. Invest. 81:461–465.

Tenenhouse H S and Jones G. 1990, Abnormal regulation of renal vitamin D catabolism by dietary phosphate in murine X-linked hypophosphatemic rickets. J. Clin. Invest. 85,1450–1455.

Tenenhouse H S at al, Am J. Physiol 1998, October 275:4 Pt 2 F527–34

Thorsett, E. D. and Wyvratt, M. J.: Inhibition of zinc peptidases that hydrolyse neuropeptides. In Neuropeptides and their Peptidases, ed. by A. J. Turner, pp. 229–292, Harwood, Chichester, UK, 1987.

Turner, A. J. (1997). Endothelin-converting enzymes. In Cell-surface peptidases in health and disease. A. J. Kenny and C. M. Boustead, eds. (Oxford, UK: BIOS Scientific Publishers Ltd.), pp.137–153.

Turner, A. J. and Tanzawa, K. (1997b). Mammalian membrane metallopeptdases: NEP, ECE, KELL, and PEX. FASEB J. II, 355–364.

Vallee, B. L. and Auld, D. S.: Zinc coordinating function and structure of zinc enzymes and other proteins. Biochemistry 29: 5647–5659, 1990.

Xiao, Z. S. Crenshaw, M., Guo, R., Nesbitt, T., Drezner, M. K., and Quarles, L. D. (1998). Intrinsic mineralization defect in Hyp mouse osteoblasts. Am.J.Physiol.Endocrinol.Metab. 275, E700-E708

Yang, X. F. Crine, P., and Boileau, G. (1995). The nature of topogenic sequences determines the transport competence of topological mutants of neutral endopeptidase-24.11. Biochem.J. 312, 99–105.

We claim:

1. A soluble purified Phosphate Regulating Gene with Homologies to Endopeptidases on the X Chromosome enzyme (secPHEX) having the amino acid sequence as set forth in SEQ ID NO:1, modified so that amino acid residues located from position 27 to position 46 inclusively have been replaced by the amino acid residues as set forth in SEQ ID NO: 4.

2. A variant secPHEX consisting of the secPHEX of claim 1 wherein the glutamic acid residue corresponding to position 581 of SEQ ID NO: 1 has been substituted with a valine residue.

3. An antigenic composition, which comprises the secPHEX of claim 1.

4. A composition comprising the secPHEX of claim 1 and a pharmaceutically acceptable carrier.

5. A composition comprising the secPHEX of claim 2 and a pharmaceutically acceptable carrier.

6. A method for obtaining a Phosphate Regulating Gene with Homologies to Endopeptidases on the X chromosome (PHEX) ligand comprising the steps of:
   contacting a sample containing one or more molecules with a secPHEX as defined in claim 2 under conditions such that binding of said one or more molecules with PHEX can occur;
   detecting said binding as an indication of the presence of a PHEX ligand in said sample; and
   selecting said PHEX ligand.

7. The method of claim 6, wherein said ligand is a PHEX inhibitor or substrate.

* * * * *